United States Patent
Wipf et al.

(10) Patent No.: US 9,217,000 B2
(45) Date of Patent: Dec. 22, 2015

(54) TARGETED NITROXIDE AGENTS

(75) Inventors: Peter Wipf, Pittsburgh, PA (US); Marie-Celine Frantz, Vaujours (FR)

(73) Assignee: Univerisyt of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/000,173

(22) PCT Filed: Feb. 17, 2012

(86) PCT No.: PCT/US2012/025586
§ 371 (c)(1),
(2), (4) Date: Aug. 16, 2013

(87) PCT Pub. No.: WO2012/112851
PCT Pub. Date: Aug. 23, 2012

(65) Prior Publication Data
US 2014/0018317 A1   Jan. 16, 2014

Related U.S. Application Data

(60) Provisional application No. 61/474,915, filed on Apr. 13, 2011, provisional application No. 61/454,003, filed on Mar. 18, 2011, provisional application No. 61/444,492, filed on Feb. 18, 2011.

(51) Int. Cl.
*C07D 451/14* (2006.01)
*C07D 211/94* (2006.01)
(Continued)

(52) U.S. Cl.
CPC .............. *C07F 5/022* (2013.01); *C07D 211/94* (2013.01); *C07D 295/24* (2013.01); *C07D 451/14* (2013.01); *C07D 471/08* (2013.01)

(58) Field of Classification Search
CPC .. C07D 451/14; C07D 211/94; C07D 471/08; C07D 295/24; C07F 5/022

USPC ............................................ 514/329; 546/244
See application file for complete search history.

(56) References Cited

U.S. PATENT DOCUMENTS 7,528,174 B2   5/2009   Wipf et al.
7,718,603 B1   5/2010   Wipf et al.
(Continued)

FOREIGN PATENT DOCUMENTS

WO   WO 2010/009405   1/2010
WO   WO 2010/141824   12/2010

OTHER PUBLICATIONS

Schirlin; Tetrahedron, 1996, 52, 305-318.*
(Continued)

*Primary Examiner* — John Mabry
*Assistant Examiner* — Daniel Carcanague
(74) *Attorney, Agent, or Firm* — Klarquist Sparkman, LLP

(57) ABSTRACT

A compound having a structure of:

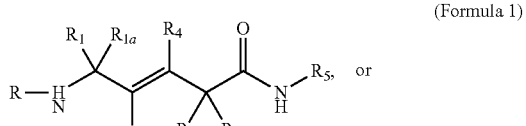

(Formula 1)

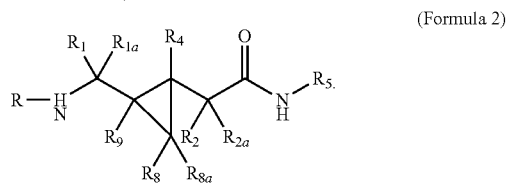

(Formula 2)

17 Claims, 5 Drawing Sheets

(51) Int. Cl.
*C07D 471/08* (2006.01)
*C07D 295/24* (2006.01)
*C07F 5/02* (2006.01)

(56) References Cited

U.S. PATENT DOCUMENTS

| | | | |
|---|---|---|---|
| 8,288,551 | B2 | 10/2012 | Wipf et al. |
| 8,609,850 | B2 * | 12/2013 | Wipf et al. ............... 546/242 |
| 2007/0161544 | A1 | 7/2007 | Wipf et al. |
| 2007/0161573 | A1 | 7/2007 | Wipf et al. |
| 2008/0308426 | A1 | 12/2008 | Krasutsky et al. |
| 2011/0039792 | A1 | 2/2011 | Wipf et al. |
| 2011/0172214 | A1 | 7/2011 | Wipf et al. |
| 2012/0004263 | A1 | 1/2012 | Niedernhofer et al. |
| 2012/0207687 | A1 | 8/2012 | Falo et al. |

OTHER PUBLICATIONS

Heimgartner Angew. Chem. Int. Ed. Engl. 1991, 30, 238-264.*
Hagmann; J. Med. Chem. 2008, 51, 4359-4369.*
Fink et al., "Hemigramicidin-TEMPO conjugates: Novel mitochondria-targeted anti-oxidants," *Biochemical Pharmacology* 74(6):801-809, Sep. 15, 2007.
Hahn et al., "Tempol, a Stable Free Radical, Is a Novel Murine Radiation Protector," *Cancer Research* 52:1750-1753, 1992.
Jiang et al., "Structural Requirements for Optimized Delivery, Inhibition of Oxidative Stress, and Antiapoptotic Activity of Targeted Nitroxides," *The Journal of Pharmacology and Experimental Therapeutics* 320(3):1050-1060, Mar. 1, 2007.
Macias et al., "Treatment with a Novel Hemigramicidin-TEMPO Conjugate Prolongs Survival in a Rat Model of Lethal Hemorrhagic Shock," *Annals of Surgery* 245(2):305-314, Feb. 1, 2007.
Mitchell et al., "Radiation, Radicals, and Images," *Annals New York Academy of Sciences* 899:28-43, 2000.
Wipf et al., "Convergent Approach to ($E$)-Alkene and Cyclopropane Peptide Isosteres," *Organic Letters* 7(1):103-106, 2005.
Wipf et al., "Mitochondrial Targeting of Selective Electron Scavengers: Synthesis and Biological Analysis of Hemigramicidin-TEMPO Conjugates," *JACS* 127(36):12460-12461, Sep. 1, 2005 (Published online Aug. 15, 2005).
European Supplemental Search Report from corresponding European Application No. 09798808.3 dated Feb. 22, 2012.
International Search Report from PCT Application No. PCT/US2009/051004, mailed Mar. 12, 2010.
Written Opinion of the International Search Authority from PCT Application No. PCT/US2009/051004, mailed Mar. 12, 2010.
International Preliminary Report on Patentability from PCT Application No. PCT/US2009/051004, dated Jan. 18, 2011.
International Search Report from corresponding international PCT Application No. PCT/US2012/025586 dated Sep. 21, 2012.
Written Opinion of the International Searching Authority from corresponding international PCT Application No. PCT/US2012/025586 dated Sep. 21, 2012.
Frantz, "Large-scale asymmetric synthesis of the bioprotective agent JP4-039 and analogs," *Org Lett.* 13 (9): 2318-2321, May 6, 2011.
Frantz, "Novel Non Peptide-Nitroxide Conjugates for targeting Mitochondria," ACS 239th National Meeting, Mar. 25, 2010.

* cited by examiner

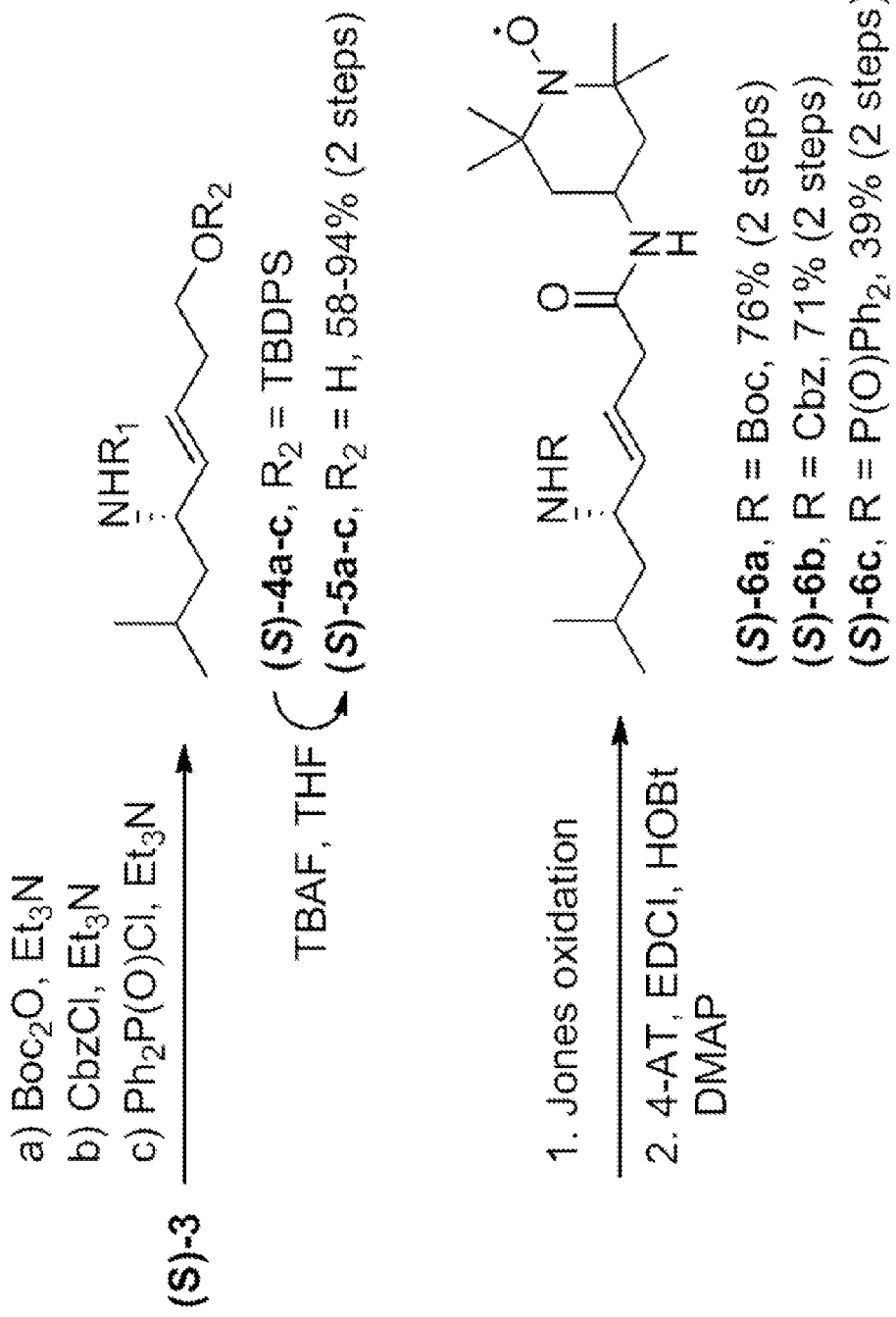

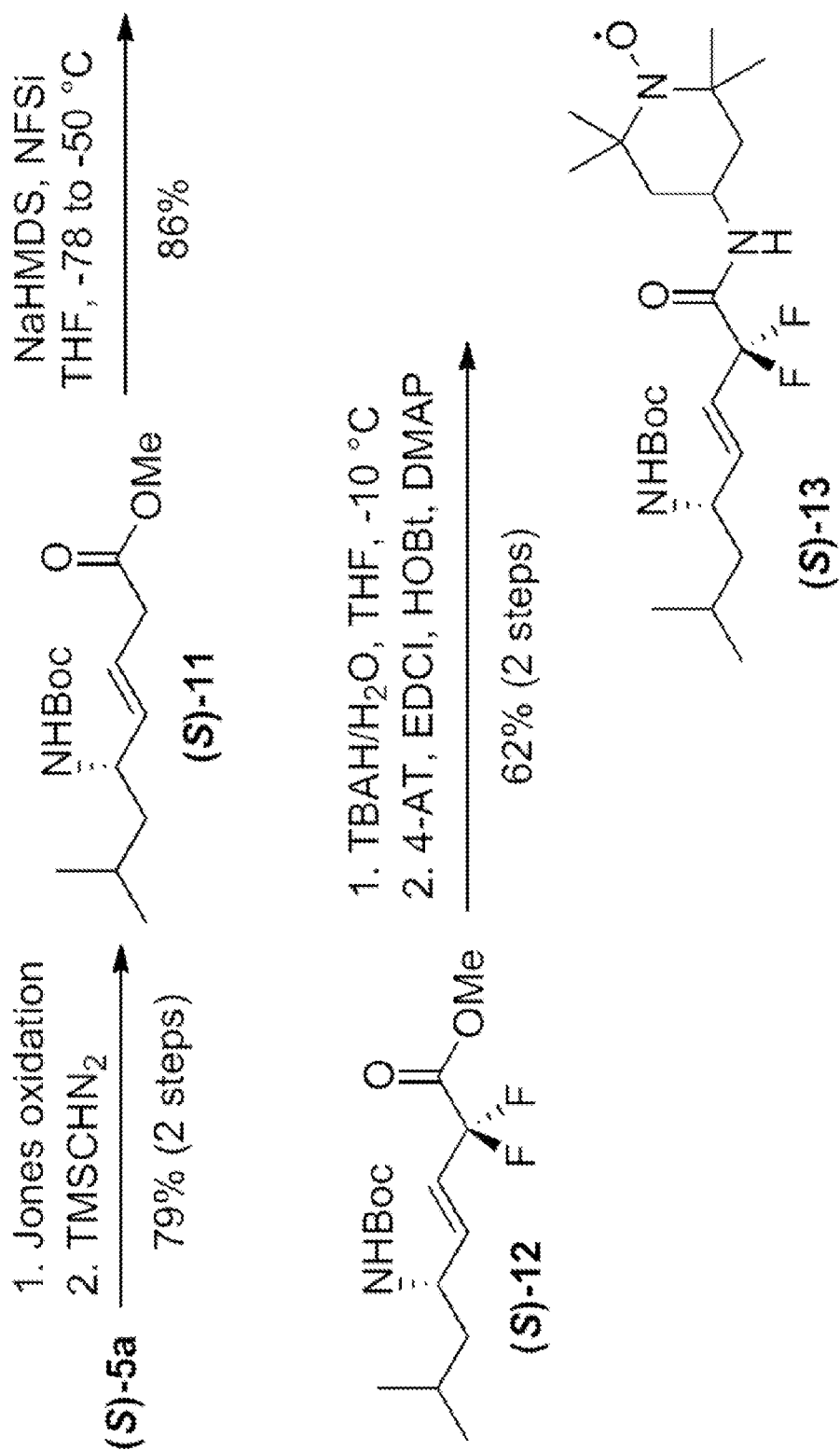
FIG. 5 Synthesis of the difluoro analog (S)-13

US 9,217,000 B2

TARGETED NITROXIDE AGENTS

CROSS REFERENCE TO RELATED APPLICATIONS

This is the U.S. National Stage of International Application No. PCT/US2012/025586, filed Feb. 17, 2012, which was published in English under PCT Article 21(2), which in turn claims the benefit of U.S. Provisional Application No. 61/444,492, filed Feb. 18, 2011, U.S. Provisional Application No. 61/454,003, filed Mar. 18, 2011, and U.S. Provisional Application No. 61/474,915, Apr. 13, 2011, all of which are incorporated herein by reference in their entireties.

ACKNOWLEDGMENT OF GOVERNMENT SUPPORT

This invention was made with government support under grant number AI068021 and grant number GM067082 awarded by the National Institutes of Health, Department of Health and Human Services. The government has certain rights in the invention.

BACKGROUND

Provided herein are novel compounds and compositions of matter comprising a nitroxide group-containing cargo (or "nitroxide containing group") and a mitochondria-targeting group (or "targeting group"). The targeting group is believed, without any intent to be bound, to have the ability to preferentially deliver the composition to mitochondrial, delivering the antioxidant and free-radical scavenging activity of the nitroxide group to cells, including but not limited to an enrichment in mitochondria. These compounds are useful, generally, for their antioxidant, electron scavenging and free-radical scavenging capacity, and, more specifically, for example and without limitation, for their radioprotective and radiomitigative abilities and the prevention as well as mitigation of degenerative diseases.

Oxidative stress in cells typically manifests itself by way of generating reactive oxygen species ("ROS") and reactive nitrogen species ("RNS"). Specifically, the cellular respiration pathway generates ROS and RNS within the mitochondrial membrane of the cell, see Kelso et al., Selective Targeting of a Redox-active Ubiquinone to Mitochondria within Cells: Antioxidant and Antiapoptotic Properties, J Biol. Chem. 276:4588 (2001). Reactive oxygen species include free radicals, reactive anions containing oxygen atoms, and molecules containing oxygen atoms that can either produce free radicals or are chemically activated by them. Specific examples include superoxide anion, hydroxyl radical, and hydroperoxides. In many disease states, the normal response to ROS and RNS generation is impaired.

Naturally occurring enzymes, such as superoxide dismutase ("SOD") and catalase salvage ROS and RNS radicals to allow normal metabolic activity to occur. Significant deviations from cell homeostasis, such as hemorrhagic shock, lead to an oxidative stress state, thereby causing "electron leakage" from the mitochondrial membrane. This "electron leakage" produces an excess amount of ROS for which the cell's natural antioxidants cannot compensate. Specifically, SOD cannot accommodate the excess production of ROS associated with hemorrhagic shock which ultimately leads to premature mitochondria dysfunction and cell death via apoptosis, see Kentner et al., Early Antioxidant Therapy with TEMPOL during Hemorrhagic Shock Increases Survival in Rats, J Trauma Inj Infect Crit. Care., 968 (2002).

Cardiolipin ("CL") is an anionic phospholipid exclusively found in the inner mitochondrial membrane of eukaryotic cells, see Iverson, S. L. and S. Orrenius, The cardiolipin cytochrome C interaction and the mitochondria) regulation of apoptosis, Arch Biochem. 423:37-46 (2003). Under normal conditions, the pro-apoptotic protein cytochrome C is anchored to the mitochondrial inner membrane by binding with CL, see Tuominen, E. K. J., et al. Phospholipid cytochrome C interaction: evidence for the extended lipid anchorage, J Biol. Chem., 277:8822-8826 (2002). The acyl moieties of CL are susceptible to peroxidation by reactive oxygen species. When ROS are generated within mitochondria in excess quantities, cytochrome C bound to CL can function as an oxidase and induces extensive peroxidation of CL in the mitochondrial membrane, see Kagan, V. E. et al., Cytochrome C acts as a cardiolipin oxygenase required, for release of proapoptotic, factors, Nat Chem Biol. 1:223-232 (2005); also Kagan, V. E. et al., Oxidative lipidomics of apoptosis: redox catalytic interactions of cytochrome c with cardiolipin and phosphatidylserine, Free Rad Biol Med. 37:1963-1985 (2005).

The peroxidation of the CL weakens the binding between the CL and cytochrome C, see Shidoji, Y. et al., Loss of molecular interaction between cytochrome C and cardiolipin due to lipid peroxidation, Biochem Biophys Res Comm. 264: 343-347 (1999). This leads to the release of the cytochrome C into the mitochondrial intermembrane space, inducing apoptotic cell death. Further, the peroxidation of CL has the effect of opening the mitochondrial permeability transition pore ("MPTP"), see Dolder, M. et al., Mitochondria creatine kinase in contact sites: Interaction with porin and adenine nucleotide translocase, role in permeability transition and sensitivity to oxidative damage, Biol Sign Recept., 10:93-111 (2001); also Imai, H. et al., Protection from inactivation of the adenine nucleotide translocator during hypoglycaemia-induced apoptosis by mitochondria/phospholipid hydroperoxide glutathione peroxidase, Biochem J., 371:799-809 (2003). Accordingly, the mitochondrial membrane swells and releases the cytochrome C into the cytosol. Excess cytochrome C in the cytosol leads to cellular apoptosis, see Iverson, S. L. et al. The cardiolipin-cytochrome C interaction and the mitochondria regulation of apoptosis, Arch Biochem Biophys. 423:37-46 (2003).

Moreover, mitochondrial dysfunction and cell death may ultimately lead to multiple organ failure despite resuscitative efforts or supplemental oxygen supply, see Cairns, C., Rude Unhinging of the Machinery of Life: Metabolic approaches to hemorrhagic Shock, Curr Crit. Care., 7:437 (2001). Accordingly, there is a need in the art for an antioxidant which scavenges escaping electrons and the ROS, thereby reducing oxidative stress. Reduction of oxidative stress delays, even inhibits, physiological conditions that otherwise might occur, such as hypoxia.

Also, there is a need to improve the permeability of antioxidants' penetration of the cellular membrane. One of the limitations of SOD is that it cannot easily penetrate the cell membrane. However, nitroxide radicals, such as TEMPO (2,2,6,6-tetramethylpiperidine-N-oxyl) and its derivatives, have been shown to penetrate the cell membrane better than SOD. Further, nitroxide radicals like, for example and without limitation, TEMPO prevent the formation of ROS, particularly superoxide, due to their reduction by the mitochondrial electron transport chain to hydroxylamine radical scavengers, see Wipf, P. et al., Mitochondria targeting of selective electron scavengers: synthesis and biological analysis of hemigramicidin-TEMPO conjugates, J Am Chem Soc. 127:12460-12461. Accordingly, selective delivery of TEMPO derivatives may lead to a therapeutically beneficial reduction of ROS and may delay or inhibit cell death due to the reduction of oxidative stress on the cell.

Selective delivery may be accomplished by way of a number of different pathways—e.g., by a biological or chemical moiety having a specific targeting sequence for penetration of the cell membrane, ultimately being taken up by the mitochondrial membrane. Selective delivery of a nitroxide SOD mimic into the mitochondrial membrane has proven difficult. Accordingly, there is a need in the art for effective and selective delivery of antioxidants that specifically target the mitochondria and its membranes as well as inter-membrane space to help reduce the ROS and RNS species. The antioxidants also help prevent cellular and mitochondria apoptotic activity which often results due to increased ROS species, see Kelso et al., Selective Targeting of a Redox-active Ubiquinone to Mitochondria within Cells: Antioxidant and Antiapoptotic Properties, J Biol Chem., 276: 4588 (2001). Examples of mitochondria-targeting antioxidants are described in United States Patent Publication Nos. 20070161573 and 20070161544.

There remains a very real need for a composition and associated methods for delivering cargo of various types to mitochondria. In one embodiment, a composition comprising membrane active peptidyl fragments having a high affinity with the mitochondria linked to cargo is provided. The cargo may be selected from a large group of candidates. There is a need for compositions and methods for effectively treating a condition that is caused by excessive mitochondria production of ROS and RNS in the mitochondrial membrane. There also is a need for compounds that can protect cells and tissues of animals against radiation damage.

The biologic consequences of exposure to ionizing radiation (IR) include genomic instability and cell death (Little J B, Nagasawa H, Pfenning T, et al. Radiation-induced genomic instability: Delayed mutagenic and cytogenetic effects of X rays and alpha particles. Radiat Res 1997; 148:299-307). It is assumed that radiolytically generated radicals are the primary cause of damage from IR. Direct radiolysis of water and the secondary reactive intermediates with a short lifetime ($10^{-10}$-$10^{-6}$ seconds) mediate the chemical reactions that trigger the damage of cellular macromolecules, including DNA and proteins, as well as phospholipids in membranes (Mitchell J B, Russo A, Kuppusamy P, et al. Radiation, radicals, and images. Ann N Y Acad Sci 2000; 899:28-43). The DNA is believed to be the primary target for the radical attack, resulting in single and double DNA strand breaks (Bryant P E. Enzymatic restriction of mammalian cell DNA: Evidence for double-strand breaks as potentially lethal lesions. Int J Radiat Biol 1985; 48:55-60). To maintain the genomic integrity, multiple pathways of DNA repair and cell-cycle checkpoint control are activated in response to irradiation-induced DNA damage (Elledge S J. Cell cycle checkpoints: Preventing an identity crisis. Science 1996; 274:1664-1672). Failure of these repair and regulatory systems leads to genotoxicity, malignant transformation, and cell death (Sachs R K, Chen A M, Brenner D J. Proximity effects in the production of chromosome aberrations by ionizing radiation. Int J Radiat Biol 1997; 71:1-19).

One of the major mechanisms of IR-induced cell death is apoptosis, most commonly realized through a mitochondria-dependent intrinsic pathway (Newton K, Strasser A. Ionizing radiation and chemotherapeutic drugs induce apoptosis in lymphocytes in the absence of Fas or FADD/MORT1 signaling. Implications for cancer therapy. J Exp Med 2000; 191: 195-200). The latter includes permeabilization of mitochondria followed by the release of cytochrome (cyt) c and other proapoptotic factors (Smac/Diablo [second mitochondrial-derived activator of caspase/direct inhibitor of apoptosis-binding protein with low pI], EndoG [endonuclease G], Omi/HtrA2, and AIF [apoptosisinducing factor]) into the cytosol as the key events in the execution of the death program. The released cyt c facilitates the formation of apoptosomes by interacting with apoptotic protease activating factor 1 (Apaf-1) and then recruits and activates procaspase-9 and triggers the proteolytic cascade that ultimately leads to cell disintegration. Release of proapoptotic factors and caspase activation designate the commencement of irreversible stages of apoptosis. Therefore, significant drug discovery efforts were directed toward the prevention of these events, particularly of the mitochondrial injury representing an important point of no return (Szewczyk A, Wojtczak L. Mitochondria as a pharmacological target. Pharmacol Rev 2002; 54:101-127). However, the exact mechanisms of cyt c release from mitochondria are still poorly understood. It was postulated that generation of reactive oxygen species (ROS), likely by means of disrupted electron transport, has a crucial role in promoting cyt c release from mitochondria (Kowaltowski A J, Castilho R F, Vercesi A E. Opening of the mitochondrial permeability transition pore by uncoupling or inorganic phosphate in the presence of Ca2+ is dependent on mitochondrial-generated reactive oxygen species. FEBS Lett 1996; 378:150-152). Notably, ROS can induce mitochondria membrane permeabilization both in vitro and in vivo, and the mitochondrial membrane transition pore was shown to be redox sensitive (Kroemer G, Reed J C. Mitochondrial control of cell death. Nat Med 2000; 6:513-519).

Conversely, antioxidants and reductants, overexpression of manganese superoxide dismutase (MnSOD) (Wong G H, Elwell J H, Oberley L W, et al. Manganous superoxide dismutase is essential for cellular resistance to cytotoxicity of tumor necrosis factor. Cell 1989; 58:923-931), and thioredoxin (Iwata S, Hori T, Sato N, et al. Adult T cell leukemia (ATL)-derived factor/human thioredoxin prevents apoptosis of lymphoid cells induced by L-cystine and glutathione depletion: Possible involvement of thiol-mediated redox regulation in apoptosis caused by pro-oxidant state. J Immunol 1997; 158:3108-3117) can delay or inhibit apoptosis. Previous studies showed that early in apoptosis, a mitochondria-specific phospholipid-cardiolipin (CL) translocated from the inner to the outer mitochondrial membrane and activated cyt c into a CL-specific peroxidase (Fernandez M G, Troiano L, Moretti L, et al. Early changes in intramitochondrial cardiolipin distribution during apoptosis. Cell Growth Differ 2002; 13:449-455 and Kagan V E, Tyurin V A, Jiang J, et al. Cytochrome c acts as a cardiolipin oxygenase required for release of proapoptotic factors. Nat Chem Biol 2005; 1:223-232). The activated cyt C further catalyzed the oxidation of CL by using mitochondrially generated ROS (Kagan V E, Tyurin V A, Jiang J, et al. Cytochrome c acts as a cardiolipin oxygenase required for release of proapoptotic factors. Nat Chem Biol 2005; 1:223-232). Most importantly, oxidized CL is an important contributor to the release of cyt c from mitochondria (Kagan V E, Tyurin V A, Jiang J, et al. Cytochrome c acts as a cardiolipin oxygenase required for release of proapoptotic factors. Nat Chem Biol 2005; 1:223-232 and Petrosillo G, Casanova G, Matera M, et al. Interaction of peroxidized cardiolipin with rat-heart mitochondrial membranes: Induction of permeability transition and cytochrome c release. FEBS Lett 2006; 580:6311-6316), which might be attributed to changes in microenvironment for the interaction between this phospholipid and cyt C (Ott M, Robertson J D, Gogvadze V, et al. Cytochrome c release from mitochondria proceeds by a two-step process. Proc Natl Acad Sci USA 2002; 99:1259-1263 and Gamido C, Galluzzi L, Brunet M, et al. Mechanisms of cytochrome C release from mitochondria. Cell Death Differ 2006; 13:1423-1433) and/or participation of oxidized CL in the formation of mitochondrial permeability transition pores (MTP) in coordination with Bcl-2 family proteins (Bid, Bax/Bak), as well as adenine nucleotide translocator (ANT) and voltage-dependent anion channel (VDAC) (Petrosillo G, Casanova G, Matera M, et al. Interaction of peroxidized cardiolipin with rat-heart mitochondrial membranes: Induction of permeability transition and cytochrome C release. FEBS Lett 2006; 580:6311-6316 and Gonzalvez F, Gottlieb E. Cardiolipin: Setting the beat of apoptosis. Apoptosis 2007; 12:877-885). In addition to their essential role in the apoptotic signaling pathway, ROS were also implicated in perpetuation of the bystander effect (Narayanan P K, Goodwin E H, Lehnert B E. Alpha particles initiate biological production of superoxide anions and hydrogen peroxide in human cells. Cancer Res 1997; 57:3963-3971 and Iyer R, Lehnert B E. Factors underlying the cell growth-related bystander responses to alpha particles. Cancer Res 2000; 60:1290-1298) and genomic instability after irradiation exposure (Spitz D R, Azzam E I, Li J J, et al. Metabolic oxidation/reduction reactions and cellular responses to ionizing radiation: A unifying concept in stress response biology. Cancer Metastasis Rev 2004; 23:311-322; Limoli C L, Giedzinski E, Morgan W F, et al. Persistent oxidative stress in chromosomally unstable cells. Cancer Res 2003; 63:3107-3111; and Kim G J, Chandrasekaran K, Morgan W F. Mitochondrial dysfunction, persistently elevated levels of reactive oxygen species and radiation-induced genomic instability: A review. Mutagenesis 2006; 21:361-367). Hence, elimination of intracellular ROS, particularly its major source, mitochondrial ROS, by antioxidants may be an important opportunity for developing radioprotectors and radiomitigators. Protection by antioxidants against IR has been studied for more than 50 years (Weiss J F, Landauer M R. Radioprotection by antioxidants. Ann N Y Acad Sci 2000; 899:44-60).

One of the major mechanisms of ionizing irradiation induced cell death is apoptosis, most commonly realized through a mitochondria dependent intrinsic pathway. Oxidation of cardiolipin catalyzed by cytochrome c, release of cytochrome c and other pro-apoptotic factors into the cytosol and subsequent caspase activation are the key events in the execution of the death program designating the commencement of irreversible stages of apoptosis.

In Belikova, N A, et al., (Cardiolipin-Specific Peroxidase Reactions of Cytochrome C in Mitochondria During Irradiation-Induced Apoptosis, Int. J. Radiation Oncology Biol. Phys 2007, 69(1): 176-186), a small interfering RNA (siRNA) approach was used to engineer HeLa cells with lowered contents of cyt c (14%, HeLa 1.2 cells). Cells were treated by γ-irradiation (in doses of 5-40 Gy). Lipid oxidation was characterized by electrospray ionization mass spectrometry analysis and fluorescence highperformance liquid chromatography-based Amplex Red assay. Release of a proapoptotic factor (cyt c, Smac/DIABLO) was detected by Western blotting. Apoptosis was revealed by caspase-3/7 activation and phosphatidylserine externalization. They showed that irradiation caused selective accumulation of hydroperoxides in cardiolipin (CL) but not in other phospholipids. HeLa 1.2 cells responded by a lower irradiation-induced accumulation of CL oxidation products than parental HeLa cells. Proportionally decreased release of a proapoptotic factor, Smac/DIABLO, was detected in cyt c-deficient cells after irradiation. Caspase-3/7 activation and phosphatidylserine externalization were proportional to the cyt c content in cells. They concluded that cytochrome C is an important catalyst of CL peroxidation, critical to the execution of the apoptotic program. This new role of cyt c in irradiation-induced apoptosis is essential for the development of new radioprotectors and radiosensitizers.

Significant drug discovery efforts have been directed towards prevention of these events, particularly of the mitochondrial injury that represents an important point of no return. Although the exact mechanisms are still not well understood, generation of reactive oxygen species (ROS) and oxidation of cardiolipin by the peroxidase function of cytochrome C/cardiolipin complexes are believed to play a critical role in promoting cytochrome C release from mitochondria. ROS—superoxide radicals dismutating to $H_2O_2$—feed the peroxidase cycle and facilitate accumulation of oxidized cardiolipin. Hence, elimination of intracellular ROS, particularly its major source, mitochondrial ROS, by electron and radical scavengers is a promising opportunity for developing radioprotectors and radiomitigators. Significant research has been conducted in the field of radiation protection to use antioxidants against ionizing irradiation (Weiss et al. Radioprotection by Antioxidants. Ann N Y Acad Sci 2000; 899:44-60).

A new class of antioxidants, stable nitroxide radicals, has been suggested as potent radioprotectors due to multiplicity of their direct radical scavenging properties as well as catalytic enzyme-like mechanisms (Saito et al. Two reaction sites of a spin label, TEMPOL with hydroxyl radical. J Pharm Sci 2003; 92:275-280; Mitchell et al. Biologically active metal-independent superoxide dismutase mimics. Biochemistry 1990; 29:2802-2807). TEMPOL (4-hydroxy-2,2,6,6-tetramethylpiperidine-N-oxyl) is a nitroxide whose properties as a radioprotector in vitro and in vivo have been extensively studied (Mitchell et al. Nitroxides as radiation protectors. Mil Med 2002; 167:49-50; Hahn et al. In vivo radioprotection and effects on blood pressure of the stable free radical nitroxides. Int J Radiat Oncol Biol Phys 1998; 42:839-842. Mitchell et al. Inhibition of oxygen-dependent radiation-induced damage by the nitroxide superoxide dismutase mimic, tempol. Arch Biochem Biophys 1991; 289:62-70; Hahn et al. Tempol, a stable free radical, is a novel murine radiation protector. Cancer Res 1992; 52:1750-1753). Currently, TEMPOL is in clinical trials as a topical radiation protector to prevent hair loss during cancer radiotherapy. While found promising and relatively effective, the required high millimolar concentrations of TEMPOL, mainly due to its poor partitioning into cells and mitochondria, set a limit for its broader applications (Gariboldi et al. Study of in vitro and in vivo effects of the piperidine nitroxide Tempol—a potential new therapeutic agent for gliomas. Eur J Cancer 2003; 39:829-837). In addition, it has been demonstrated that TEMPOL must be present during irradiation to exert its radioprotective effect (Mitchell et al. Radiation, radicals, and images. Ann N Y Acad Sci 2000; 899:28-43; Mitchell et al. Inhibition of oxygen-dependent radiation-induced damage by the nitroxide superoxide dismutase mimic, tempol. Arch Biochem Biophys 1991; 289: 62-70), This suggests that the protective mechanisms of TEMPOL are limited to its interactions with short-lived radiolytic intermediates produced by irradiation.

Sufficient concentrations of antioxidants at the sites of free radical generation are critical to optimized protection strategies. A great deal of research has indicated that mitochondria are both the primary source and major target of ROS (Reviewed in Orrenius S. Reactive oxygen species in mitochondria-mediated cell death. Drug Metab Rev 2007; 39:443-455). In fact, mitochondria have been long considered as an important target for drug discovery (Szewczyk et al., Mitochondria as a pharmacological target. 221 Pharmacol. Rev.

54:101-127; 2002; Garber K. Targeting mitochondria emerges as therapeutic strategy. J. Natl. Cancer Inst. 97:1800-1801; 2005).

Chemistry-based approaches to targeting of compounds to mitochondria include the use of proteins and peptides, as well as the attachment of payloads to lipophilic cationic compounds, triphenyl phosphonium phosphate, sulfonylureas, anthracyclines, and other agents with proven or hypothetical affinities for mitochondria (Murphy M P. Targeting bioactive compounds to mitochondria. Trends Biotechnol. 15:326-330; 1997; Dhanasekaran et al., Mitochondria superoxide dismutase mimetic inhibits peroxideinduced oxidative damage and apoptosis: role of mitochondrial superoxide. Free Radic. Biol. Med. 157 39:567-583; 2005; Hoye et al., Targeting Mitochondria. Acc. Chem. Res. 41: 87-97, 2008).

SUMMARY

One embodiment disclosed herein is a compound, or a pharmaceutically acceptable salt or ester thereof, having a structure of:

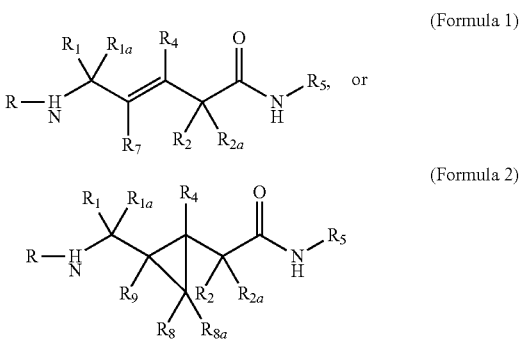

(Formula 1)

(Formula 2)

wherein $R_1$ and $R_{1a}$ are independently hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_5$ is an —N—O., —N—OH or —N=O containing group; R is —C(O)—$R_6$, —C(O)O—$R_6$, or —P(O)—$(R_6)_2$, wherein $R_6$ is $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted; $R_7$, $R_8$, $R_{8a}$, and $R_9$ are independently H or a halo; and $R_2$ and $R_{2a}$ are F.

A further embodiment disclosed herein is a compound, or a pharmaceutically acceptable salt or ester thereof, having a structure of:

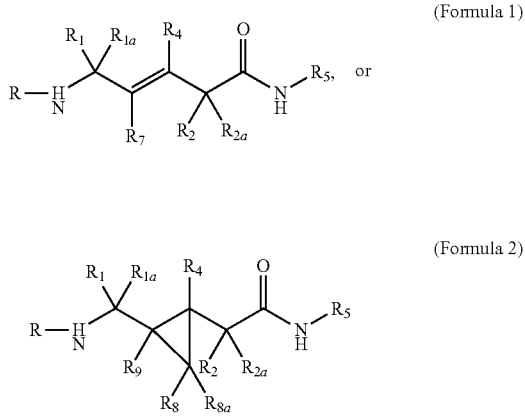

(Formula 1)

(Formula 2)

wherein $R_1$ and $R_{1a}$ are independently hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_5$ is an —N—O., —N—OH or —N=O containing group; R is —C(O)—$R_6$, —C(O)O—$R_6$, or —P(O)—$(R_6)_2$, wherein $R_6$ is $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted; $R_7$, $R_8$, $R_{8a}$, and $R_9$ are independently H or a halo; and $R_2$ and $R_{2a}$ are each a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted.

Another embodiment disclosed herein is a compound, or a pharmaceutically acceptable salt or ester thereof, having a structure of:

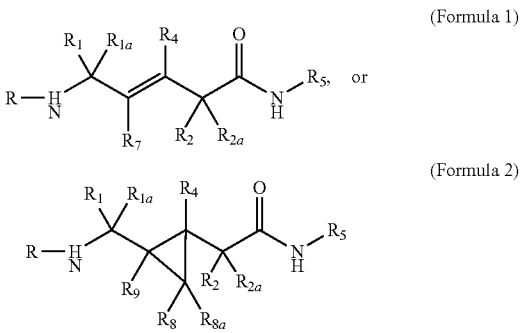

(Formula 1)

(Formula 2)

wherein $R_1$, $R_{1a}$, $R_2$, and $R_{2a}$ are independently hydrogen, a halo, a'$C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_5$ is an —N—O., —N—OH or —N=O containing group; R is —C(O)—$R_6$, —C(O)O—$R_6$, or —P(O)—($R_6$)$_2$, wherein $R_6$ is $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted; $R_8$, $R_{8a}$, and $R_9$ are independently H or a halo; and $R_7$ is a halo, a $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted.

An additional embodiment disclosed herein is a compound, or a pharmaceutically acceptable salt or ester thereof, having a structure of:

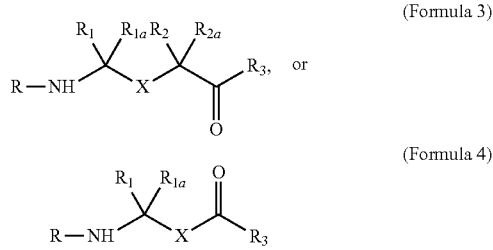

(Formula 3)

(Formula 4)

wherein X is

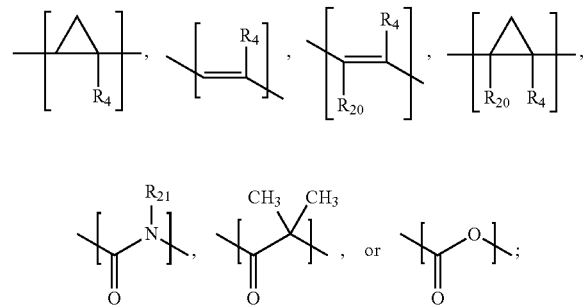

$R_1$, $R_{1a}$, $R_2$, $R_{2a}$, $R_4$, $R_{20}$ and $R_{21}$ are each independently hydrogen, halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted;

$R_3$ is —NH—$R_5$, —O—$R_5$ or —CH$_2$—$R_5$, wherein $R_5$ is an —N—O., —N—OH or —N=O containing group;

R is —C(O)—$R_6$, —C(O)O—$R_6$, or —P(O)—($R_6$)$_2$, wherein $R_6$ is $C_1$-$C_6$ straight or branched-chain alkyl optionally comprising one or more phenyl (—$C_6H_5$) groups, and that optionally are methyl-, ethyl-, hydroxyl- or fluoro-substituted;

provided that if X is:

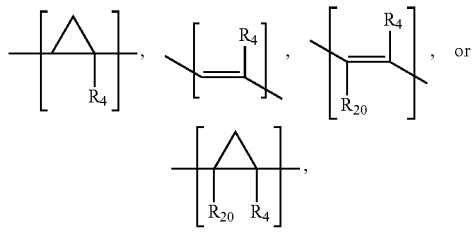

then at least one of $R_4$ or $R_{20}$ is halo, or $R_3$ is

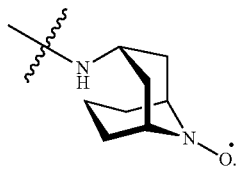

In certain embodiments, the compound is in the form of a nitroxide, or its corresponding hydroxylamine, or its corresponding nitroxonium ion.

Also disclosed herein are pharmaceutical compositions comprising any of the compounds disclosed herein, and at least one pharmaceutically acceptable additive.

Further disclosed herein is a method of preventing or treating radiation damage in a subject, comprising administering to a subject in need thereof, a therapeutically effective amount of a compound disclosed herein.

Also disclosed herein is a method of scavenging free radicals in a subject, comprising administering to a subject in need thereof, a therapeutically effective amount of a compound disclosed herein.

The foregoing will become more apparent from the following detailed description, which proceeds with reference to the accompanying figures.

BRIEF DESCRIPTION OF THE DRAWINGS

FIGS. 3-5 show a synthesis scheme for a difluoro compound disclosed herein.

DETAILED DESCRIPTION

Terminology

Figure 1:
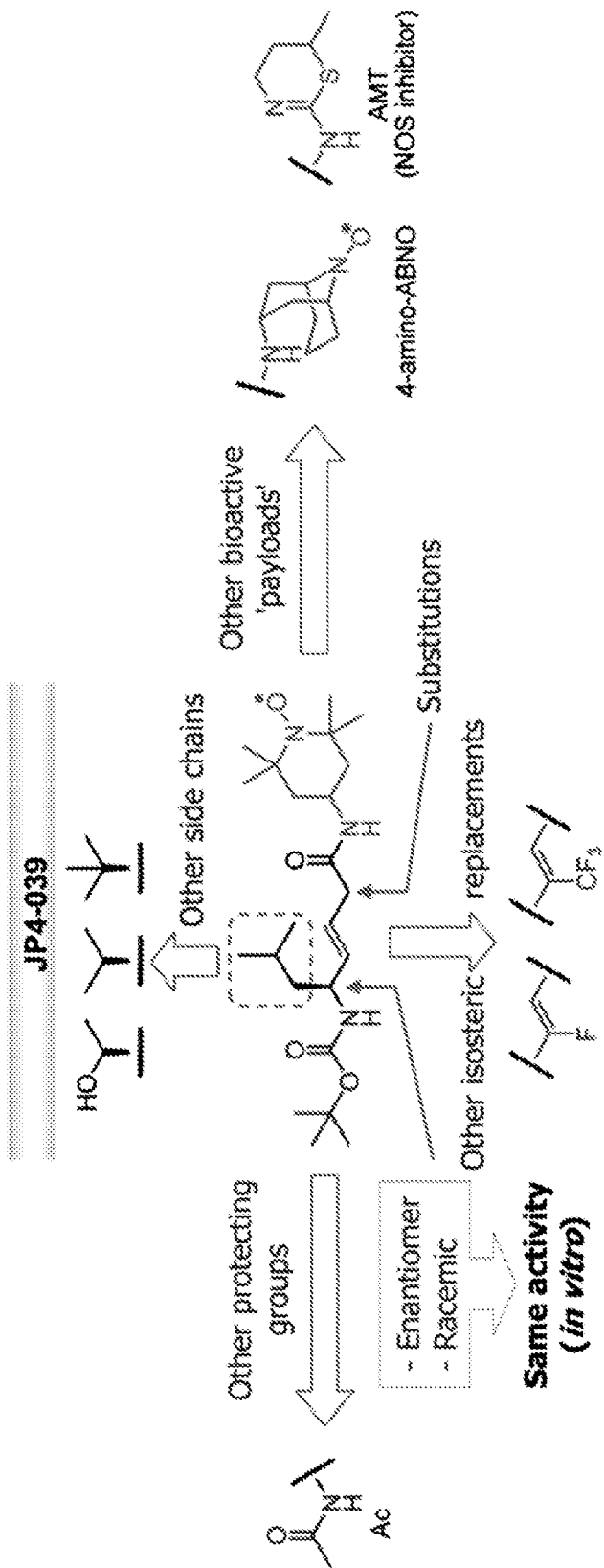
FIG. 1 depicts various structural motifs for compounds disclosed herein.

To facilitate review of the various examples of this disclosure, the following explanations of specific terms are provided:

"Administration" as used herein is inclusive of administration by another person to the subject or self-administration by the subject.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$) alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$) alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

An antioxidant compound is defined herein as a compound that decreases the rate of oxidation of other compounds or prevents a substance from reacting with oxygen or oxygen containing compounds. A compound may be determined to be an antioxidant compound by assessing its ability to decrease molecular oxidation and/or cellular sequellae of oxidative stress, for example, and without limitation, the ability to decrease lipid peroxidation and/or decrease oxidative damage to protein or nucleic acid. In one embodiment, an antioxidant has a level of antioxidant activity between 0.01 and 1000 times the antioxidant activity of ascorbic acid in at least one assay that measures antioxidant activity.

The term "halo" refers to fluoro, bromo, chloro and iodo substituents.

The term "reactive oxygen species" ("ROS") includes, but is not limited to, superoxide anion, hydroxyl, and hydroperoxide radicals.

"Substituted" or "substitution" refer to replacement of a hydrogen atom of a molecule or an R-group with one or more additional R-groups such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, nitro, sulfato or other R-groups.

The term "subject" refers to animals, including mammals (for example, humans and veterinary animals such as dogs, cats, pigs, horses, sheep, and cattle).

A "therapeutically effective amount" refers to a quantity of a specified agent sufficient to achieve a desired effect in a subject being treated with that agent. For example, a therapeutically amount may be an amount of a targeted nitroxide agent that is sufficient to prevent, ameliorate or treat radiation damage in a subject. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as cancer. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment mitigates radiation-induced damage. In particular, the mitigation reduces cellular death after potentially toxic doses of radiation, particularly after accidental exposure to radiation, and in radiation counterterrorism.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS—Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride.

Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. As used herein, unless indicated otherwise, for instance in a structure, all compounds and/or structures described herein comprise all possible stereoisomers, individually or mixtures thereof. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Compounds

Provided herein are compounds and compositions comprising a targeting group and a cargo, such as a nitroxide-containing group. The cargo may be any useful compound, such as an antioxidant, as are well known in the medical and chemical arts. The cargo may comprise a factor having anti-microbial activity. For example, the targeting groups may be cross-linked to antibacterial enzymes, such as lysozyme, or antibiotics, such as penicillin. Other methods for attaching the targeting groups to a cargo are well known in the art. In one embodiment, the cargo is an antioxidant, such as a nitroxide-containing group. In another embodiment, the cargo transported by mitochondria-selective targeting agents may include an inhibitor of NOS activity. The cargo may have a property selected from the group consisting of antioxidant, radioprotective, protective, anti-apoptotic, therapeutic, ameliorative, NOS antagonist and combinations thereof. In another embodiment, the cargo may have the ability to inhibit nitric oxide synthase enzyme activity. It will be appreciated that a wide variety of cargos may be employed in the composition described herein. Non-limiting examples of cargos include: a 2-amino-6-methyl-thiazine, a ubiquinone analog, a ubiquinone analog fragment moiety, a ubiquinone analog fragment moiety lacking a hydrophilic tail, a superoxide dismutase mimetic, a superoxide dismutase biomimetic and a salen-manganese compound.

While the generation of ROS in small amounts is a typical byproduct of the cellular respiration pathway, certain conditions, including a disease or other medical condition, may occur in the patient when the amount of ROS is excessive to the point where natural enzyme mechanisms cannot scavenge the amount of ROS being produced. Therefore, compounds, compositions and methods that scavenge reactive oxygen species that are present within the mitochondrial membrane of the cell are useful and are provided herein. These compounds, compositions and methods have the utility of being able to scavenge an excess amount of ROS being produced that naturally occurring enzymes SOD and catalase, among others, cannot cope with.

Disclosed herein in one embodiment are compounds comprising a targeting group and a cargo that is a nitroxide-containing group and compositions comprising the compounds. Compounds and compositions described herein have use in the prophylaxis and treatment of exposure to ionizing radiation, in anti-ageing therapies and, generally, in treating conditions that benefit from antioxidant treatment. Examples of these compounds are provided below and in the claims. For example, the effective mitochondrial concentration of mitochondria targeted conjugated nitroxides (—N—O, —N—OH or N=O containing compounds and groups) against γ-irradiation could be increased up to 1,000 times (and their required tissues concentrations can be reduced 1,000 times from 10 mM to 10 µM) compared with parent non-conjugated nitroxides. Enrichment in mitochondria of mitochondria targeted nitroxides has been demonstrated by EPR spectroscopy as well as by MS analysis of their content in mitochondria obtained from cells incubated with mitochondria targeted nitroxides. Delivery of mitochondria targeted-nitroxides into mitochondria does not depend on the mitochondrial membrane potential. Therefore, mitochondria targeted nitroxides can accumulate not only in intact but also in de-energized or damaged mitochondria with low membrane potential. Moreover, mitochondria targeted nitroxide conjugates are delivered into mitochondria without affecting the mitochondrial membrane potential. Hence, they do not impair the major mitochondrial function, the energy production, in cells. In addition, the conjugated nitroxides provide a new important feature, post irradiation protection.

Like other nitroxides, conjugated mitochondria targeted nitroxides might potentially lower blood pressure and sympathetic nerve activity. However, the dramatically reduced dose of mitochondria targeted nitroxides (about 1,000-fold), compared to non-conjugated parental nitroxides, may be significantly below of those inducing side effects.

According to one embodiment, the targeted nitroxide agent has a structure of:

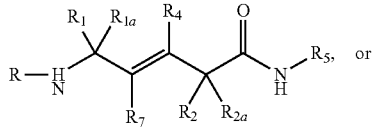

(Formula 1)

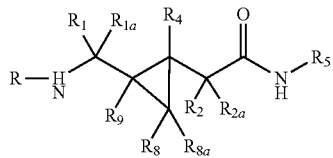

(Formula 2)

wherein $R_1$, $R_{1a}$, $R_2$, and $R_{2a}$ are independently hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_5$ is an —N—O., —N—OH or —N=O containing group; R is —C(O)—$R_6$, —C(O)O—$R_6$, or —P(O)—$(R_6)_2$, wherein $R_6$ is $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted; $R_7$, $R_8$, $R_{8a}$, and $R_9$ are independently H or a halo, and wherein the compound is not XJB-5-208.

In certain embodiments of Formula 1 or 2, $R_2$ and $R_{2a}$ are F.

In certain embodiments of Formula 1 or 2, $R_2$ and $R_{2a}$ are each a halo, $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted. In particular, $R_2$ and $R_{2a}$ are each a halo, or a $C_1$-$C_6$ straight or branched-chain alkyl.

In certain embodiments of Formula 1 or 2, $R_7$ is a halo, a $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted.

In certain embodiments of Formula 1 or 2, $R_1$ is a $C_1$-$C_6$ straight or branched-chain alkyl (particularly tert-butyl); $R_{1a}$ is H; $R_2$ and $R_{2a}$ are each independently a halo (particularly F); $R_7$ is H or a $C_1$-$C_6$ straight or branched-chain alkyl; $R_4$ is H; $R_5$ is an —N—O.— containing group; and R is —C(O)O—$R_6$ wherein $R_6$ is $C_1$-$C_6$ straight or branched-chain alkyl (particularly tert-butyl).

In certain embodiments of Formula 1 or 2, $R_5$ is

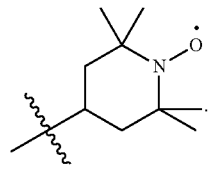 [SMILES: *C1CC(C)(C)N(O)C(C)(C)C1]

In a further embodiment, the compound has the structure:

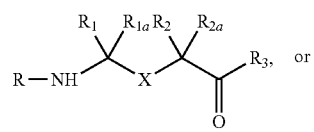

Formula 3

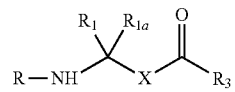

Formula 4 wherein X is

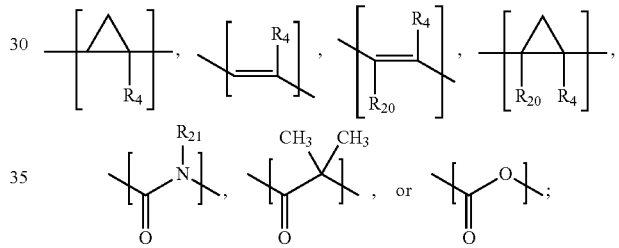

$R_1$, $R_{1a}$, $R_2$, $R_{2a}$, $R_4$, $R_{20}$ and $R_{21}$ are each independently hydrogen, halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted;

$R_3$ is —NH—$R_5$, —O—$R_5$ or —$CH_2$—$R_5$, where $R_5$ is an —N—O., —N—OH or —N=O containing group;

R is —C(O)—$R_6$, —C(O)O—$R_6$, or —P(O)—$(R_6)_2$, wherein $R_6$ is $C_1$-$C_6$ straight or branched-chain alkyl optionally comprising one or more phenyl (—$C_6H_5$) groups, and that optionally are methyl-, ethyl-, hydroxyl- or fluoro-substituted;

provided that if X is:

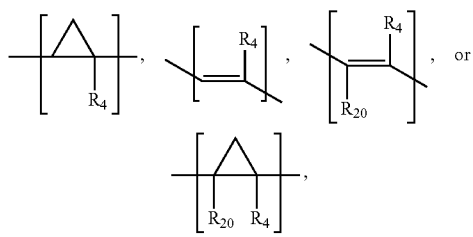

then at least one of $R_4$ or $R_{20}$ is halo, or $R_3$ is

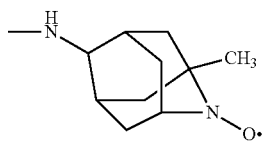

In certain embodiments of formula 3 or 4, $R_3$ is

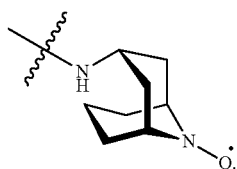

(1-Me-AZADO or 1-methyl azaadamantane N-oxyl). In other embodiments of formula 3 or 4, $R_3$ is

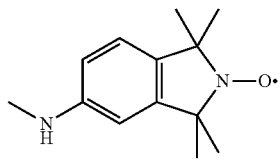

(TMIO; 1,1,3,3-tetramethylisoindolin-2-yloxyl). In certain embodiments of formula 1 or 2, $R_5$ is 1-Me-AZADO or TMIO (except that the —$NH_2$— linking group is does not constitute part of the 1-Me-AZADO or TMIO group since it is already present in the formula 1 or 2 structure).

In certain embodiments of formula 1, 2, 3 or 4, R is Ac (Acetyl, R=—C(O)—$CH_3$), Boc (R=—C(O)O-tert-butyl), Cbz (R=—C(O)O-benzyl (Bn)) groups. R also may be a diphenylphosphate group, that is, R=

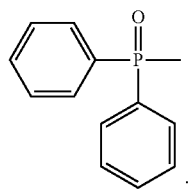

In certain embodiments of formula 3 or 4, X is

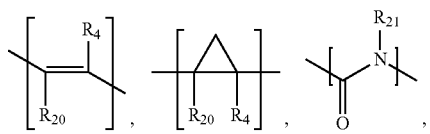

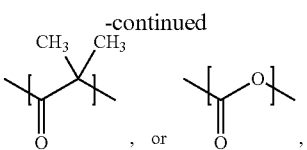

wherein at least one of $R_4$ or $R_{20}$ is a halo.

Figure 2:
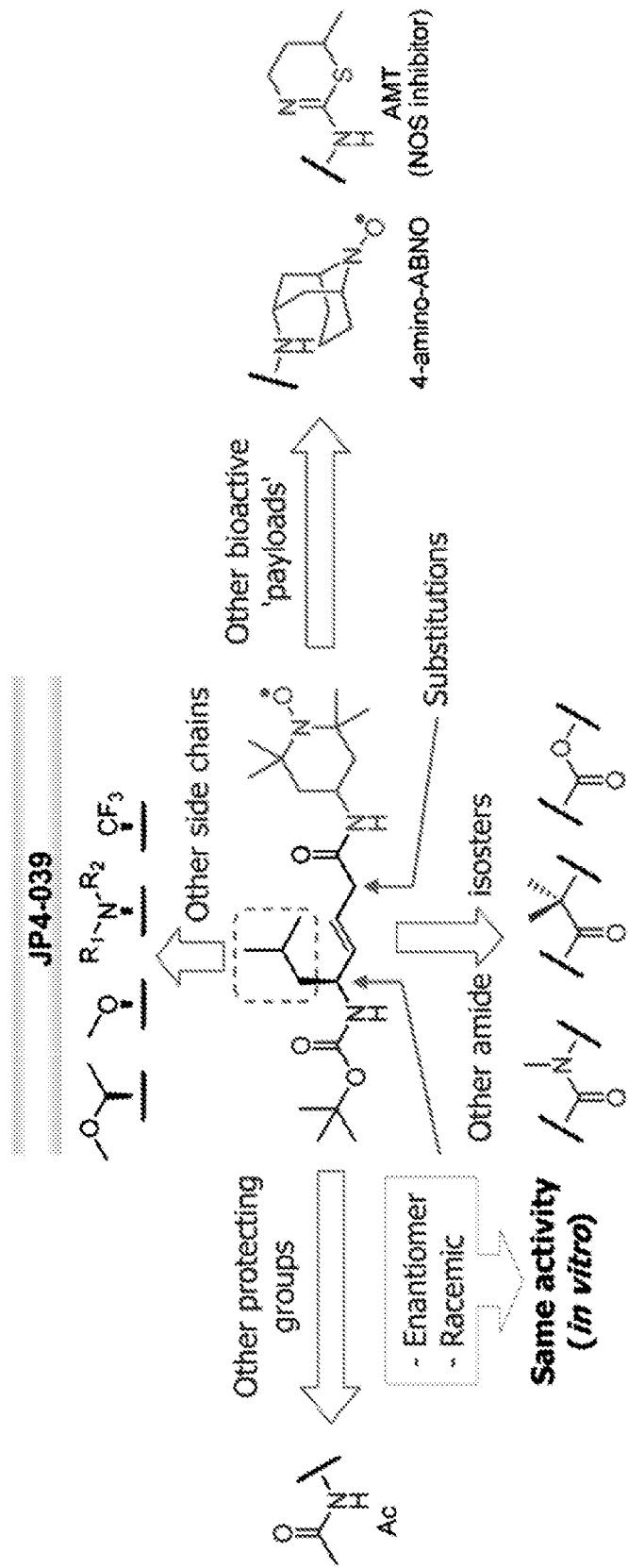
FIG. 2 depicts various structural motifs for compounds disclosed herein.

FIGS. 1 and 2 also show various structural moieties for the compounds disclosed herein.

As indicated above, $R_5$ is an —N—O., —N—OH or —N=O containing group (not —N—O., —N—OH or —N=O, but groups containing those moieties, such as TEMPO, etc, as described herein). It should be recognized that the nitroxides (—N—O.) disclosed herein may undergo reduction in vivo to their corresponding hydroxylamines (—N—OH) and/or may undergo oxidation in vivo to their corresponding nitroxonium ions. All three forms may be in equilibrium and their ratio depends on the redox environment. Any one of the three forms, or a mixture thereof, could be administered to a subject.

As is known to one ordinarily skilled in the art, nitroxide and nitroxide derivatives, including TEMPOL and associated TEMPO derivatives are stable radicals that can withstand biological environments. Therefore, the presence of the 4-amino-TEMPO, TEMPOL or another nitroxide "payload" within the mitochondria membrane can serve as an effective and efficient electron scavenger of the ROS being produced within the membrane. Non-limiting examples of this include TEMPO (2,2,6,6-Tetramethyl-4-piperidine 1-oxyl) and TEMPOL (4-Hydroxy-TEMPO), in which, when incorporated into the compound described herein, form, for example, when $R_3$ is —NH—$R_5$, —O—$R_5$:

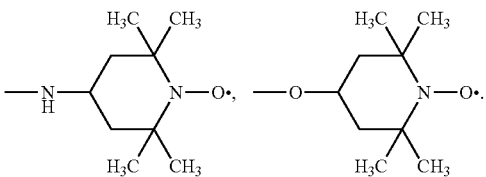

Additional non-limiting examples of —N—O., —N—OH or N=O containing group are provided in Table 1 and in FIG. 1 (from Jiang, J., et al. "Structural Requirements for Optimized Delivery, Inhibition of Oxidative Stress, and Antiapoptotic Activity of Targeted Nitroxides", J Pharmacol Exp Therap. 2007, 320(3):1050-60). A person of ordinary skill in the art would be able to conjugate (covalently attach) any of these compounds to the rest of the compound using common linkers and/or conjugation chemistries, such as the chemistries described herein. Table 1 provides a non-limiting excerpt from a list of over 300 identified commercially-available —N—O., —N—OH or N=O containing compounds that may be useful in preparation of the compounds or compositions described herein.

TABLE 1

| Structure | Commercially-available —N—O•, —N—OH or N=O containing groups | |
|---|---|---|
| | Name | CAS No. |
| (trimethylamine N-oxide structure) | Trimethylamine N-Oxide | 1184-78-7 |
| (N,N-dimethyldodecylamine N-oxide structure) | N,N-Dimethyldodecylamine N-Oxide | 1643-20-5 70592-80-2 |
| (N-benzoyl-N-phenylhydroxylamine structure) | N-Benzoyl-N-Phenylhydroxylamine | 304-88-1 |
| (N,N-diethylhydroxylamine structure) | N,N-Diethylhydroxylamine | 3710-84-7 |
| (N,N-dibenzylhydroxylamine structure) | N,N-Dibenzylhydroxylamine | 14165-27-6 621-07-8 |
| (di-tert-butyl nitroxide structure) | Di-Tert-Butyl Nitroxide | 2406-25-9 |
| (N,N-dimethylhydroxylamine hydrochloride structure) | N,N-Dimethylhydroxyl-amine Hydrochloride | 16645-06-0 |
| (metobromuron structure) | Metobromuron | 3060-89-7 |
| (benzyl-di-beta-hydroxy ethylamine-N-oxide structure) | Benzyl-Di-Beta-Hydroxy Ethylamine-N-Oxide | |
| (bis(trifluoromethyl)nitroxide structure) | Bis(Trifluoro-methyl)Nitroxide | 2154-71-4 |
| (triethylamine N-oxide structure) | Triethylamine N-Oxide | 2687-45-8 |

TABLE 1-continued

Commercially-available —N—O•, —N—OH or N=O containing groups

| Structure | Name | CAS No. |
|---|---|---|
|  | | |
| 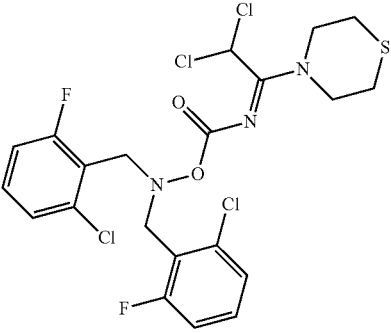 [SMILES: O=C(/N=C(\C(Cl)Cl)N1CCSCC1)ON(Cc1c(F)cccc1Cl)Cc1c(F)cccc1Cl] | N-Methoxy-N-Methylcarbamate | 6919-62-6 |
| 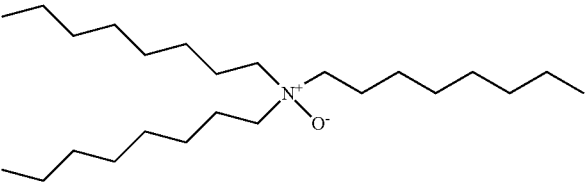 [SMILES: CCCCCCCC[N+]([O-])(CCCCCCCC)CCCCCCCC] | N,N-BIS(2-CHLORO-6-FLUOROBENZYL)-N-[(((2,2-DICHLORO-1-(1,4-THIAZINAN-4-YL+) ETHYLIDENE] AMINO)CARBONYL) OXY]AMINE | |
| 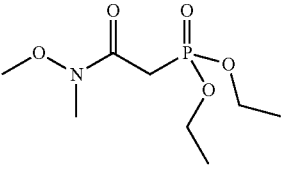 | Tri-N-Octylamine N-Oxide | 13103-04-3 |
| 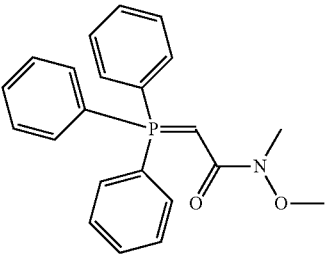 [SMILES: CON(C)C(=O)C=P(c1ccccc1)(c1ccccc1)c1ccccc1] | DIETHYL (N-METHOXY-N-METHYL-CARBAMOYL-METHYL) PHOSPHONATE | 124931-12-0 |
| 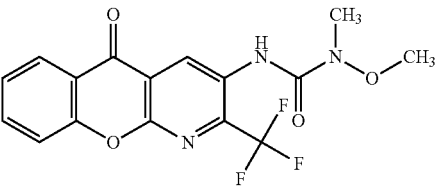 | N-Methoxy-N-Methyl-2-(Triphenyl-phosphoranylidene) Acetamide | 129986-67-0 |
| 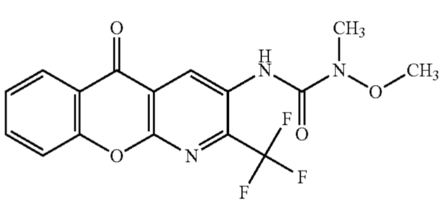 [SMILES: CON(C)C(=O)Nc1cc2c(=O)c3ccccc3oc2nc1C(F)(F)F] | N-Methoxy-N-Methyl-N'-[5-Oxo-2-(Trifluoromethyl)-5h-Chromeno[2,3-B]Pyridi+N-3-Yl]Urea | |

TABLE 1-continued

Commercially-available —N—O•, —N—OH or N═O containing groups

| Structure | Name | CAS No. |
|---|---|---|
| 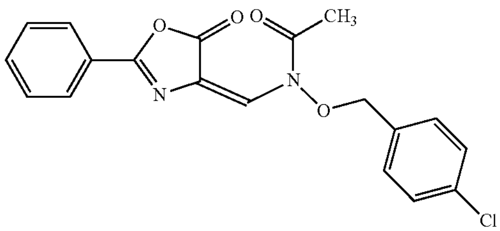 [SMILES: CC(=O)N(/C=C1/N=C(c2ccccc2)OC1=O)OCc1ccc(Cl)cc1] | N-[(4-Chlorobenzyl)Oxy]-N-([5-Oxo-2-Phenyl-1,3-Oxazol-4(5h)-Yliden]Methyl+) Acetamide | |
| 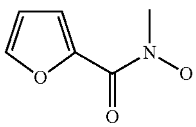 | N-Methyl-furohydroxamic Acid | 109531-96-6 |
| 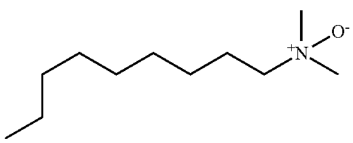 | N,N-Dimethylnonyl-amine N-Oxide | 2536-13-2 |
| 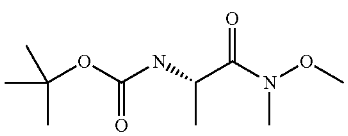 [SMILES: CON(C)C(=O)[C@H](C)NC(=O)OC(C)(C)C] | N-(Tert-Butoxycarbonyl)-L-Alanine N'-Methoxy-N'-Methylamide | 87694-49-3 |
| 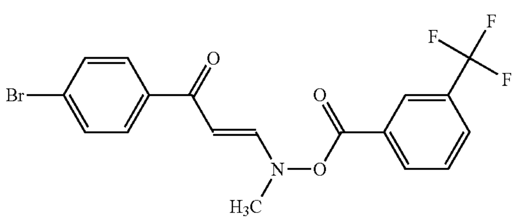 [SMILES: CN(/C=C/C(=O)c1ccc(Br)cc1)OC(=O)c1cccc(C(F)(F)F)c1] | 1-(4-Bromophenyl)-3-(Methyl([3-(Trifluoromethyl) Benzoyl]Oxy)Amino)-2-Prop+ En-1-One | |
| 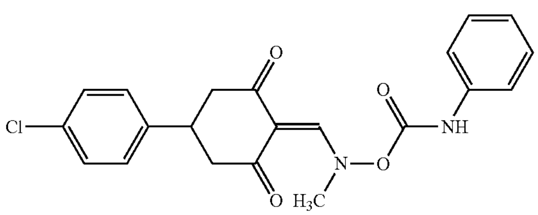 [SMILES: CN(C=C1C(=O)CC(c2ccc(Cl)cc2)CC1=O)OC(=O)Nc1ccccc1] | 2-([[(Anilinocarbonyl)Oxy](Methyl)Amino] Methylene)-5-(4-Chlorophenyl)-1,3+-Cyclohexanedione | |
| 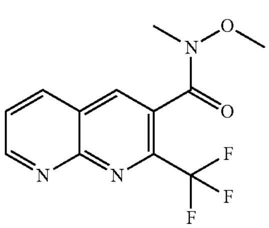 [SMILES: CON(C)C(=O)c1cc2cccnc2nc1C(F)(F)F] | N-Methoxy-N-Methyl-2-(Trifluoromethyl)-1,8-Naphthyridine-3-Carboxamide | |
| 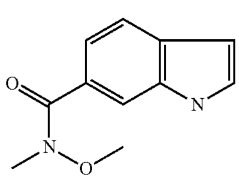 | N-Methoxy-N-Methyl-Indole-6-Carboxamide | |

TABLE 1-continued

Commercially-available —N—O•, —N—OH or N=O containing groups

| Structure | Name | CAS No. |
|---|---|---|
| [Desferrioxamin structure] | Desferrioxamin | |
| [structure] | AKOS 91254 | 127408-31-5 |
| [structure] | N-[(3s,4r)-6-Cyano-3,4-Dihydro-3-Hydroxy-2,2-Dimethyl-2h-1-Benzopyran-4-Y+L]-N-Hydroxyacetamide | 127408-31-5 |
| [structure] | N-Methoxy-N-Methyl-1,2-Dihydro-4-Oxo-Pyrrolo[3,2,1-Ij]Quinoline-5-Carboxa+Mide | |
| [structure] | Fr-900098 | |
| [structure] | 2,2'-(Hydroxyimino)Bis-Ethanesulfonic Acid Disodium Salt | 133986-51-3 |
| [structure] | Fmoc-N-Ethyl-Hydroxylamine | |

TABLE 1-continued

Commercially-available —N—O•, —N—OH or N=O containing groups

| Structure | Name | CAS No. |
|---|---|---|
| 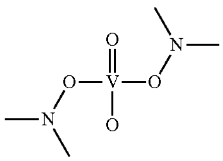 | Bis(N,N-Dimethyl-hydroxamido) Hydroxooxovanadate | |
| 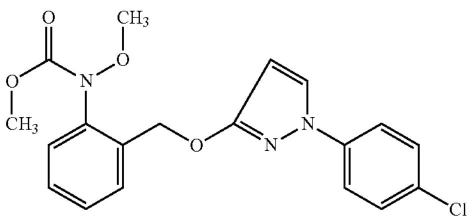 [SMILES: COC(=O)N(OC)c1ccccc1COc1ccn(-c2ccc(Cl)cc2)n1] | Pyraclostrobin | 175013-18-0 |
| 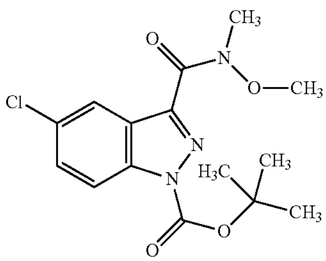 [SMILES: CON(C)C(=O)c1nn(C(=O)OC(C)(C)C)c2ccc(Cl)cc12] | 1-Boc-5-Chloro-3-(Methoxy-Methyl-Carbamoyl)Indazole | |
| 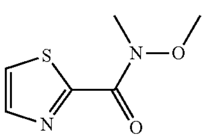 | N-Methoxy-N-Methyl-Thiazole-2-Carboxamide | |
| 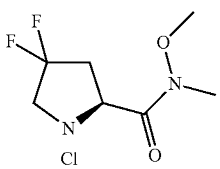 | 4,4-Difluoro-N-Methyl-N-Methoxy-L-Prolinamide Hcl | |
| 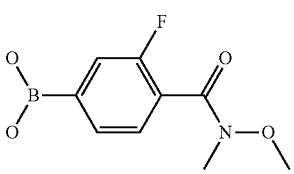 [SMILES: CON(C)C(=O)c1ccc(B(O)O)cc1F] | 3-Fluoro-4-(Methoxy(Methyl) Carbamoyl)Phenyl-boronic Acid | 913835-59-3 |
| 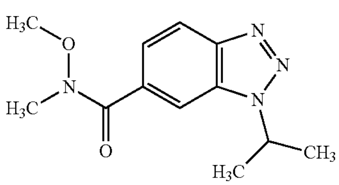 [SMILES: CON(C)C(=O)c1ccc2nnn(C(C)C)c2c1] | 1-Isopropyl-N-Methoxy-N-Methyl-1h-Benzo[D][1,2,3]Triazole-6-Carboxamide | 467235-06-9 |
| 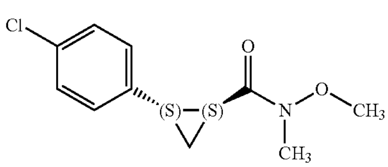 | (Trans)-2-(4-Chlorophenyl)-N-Methoxy-N-Methylcyclopropane carboxamide | |

TABLE 1-continued

Commercially-available —N—O•, —N—OH or N=O containing groups

| Structure | Name | CAS No. |
|---|---|---|
| 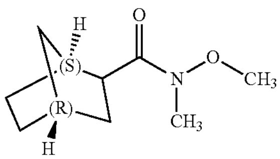 | Bicyclo[2.2.1]Heptane-2-Carboxylic Acid Methoxy-Methyl-Amide | |
| 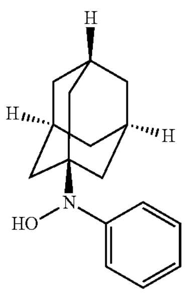 [SMILES: ON(c1ccccc1)[C@]12C[C@H]3C[C@H](C[C@H](C3)C1)C2] | Akos Bc-0582 | |
| 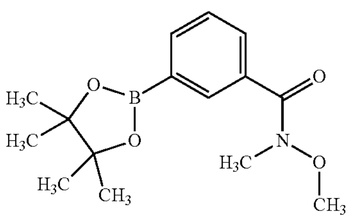 | 3-(N,O-Dimethylhydroxyl-aminocarbonyl)Phenylboronic Acid, Pinacol Ester | |
| 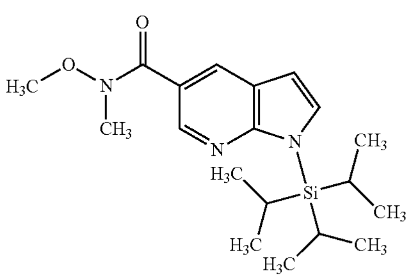 [SMILES: CON(C)C(=O)c1cnc2c(ccn2[Si](C(C)C)(C(C)C)C(C)C)c1] | 1-Triisopropylsilanyl-1h-Pyrrolo[2,3-B]Pyridine-5-Carboxylic Acid Methoxy+-Methyl-Amide | |

The compounds described above can be synthesized by any useful method. The compounds may be synthesized by the following steps:

A. reacting an aldehyde of structure $R_1$—C(O)—, wherein, for example and without limitation, $R_1$ is $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl, with (R)-2-methylpropane-2-sulfinamide to form an imine, for example

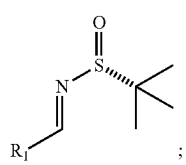

B. reacting a terminal alkyne-1-ol (CHC—$R_2$—C—OH), wherein, for example and without limitation, $R_2$ is not present or is branched or straight-chained alkylene, including methyl, ethyl, propyl, etc., with a tert-butyl)diphenyl-silane salt to produce an alkyne, for example

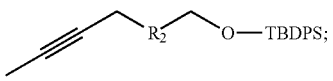

C. reacting (by hydrozirconation) the alkyne with the imine in the presence of an organozirconium catalyst to produce an alkene, for example

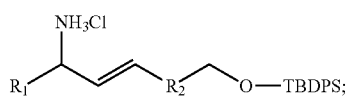

D1. acylating the alkene to produce a carbamate, for example

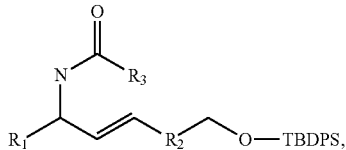

wherein, for example and without limitation, $R_3$ is $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl;

D2. optionally, cyclopropanating the alkene and then acylating the alkene to produce a carbamate, for example

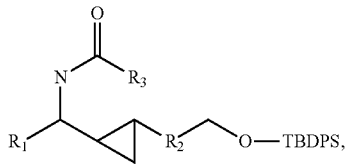

wherein, for example and without limitation, $R_3$ is $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl;

E. removing the t-butyldiphenylsilyl group from the carbamate to produce an alcohol, for example

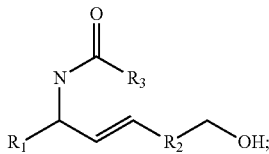

F. oxidizing the alcohol to produce a carboxylic acid, for example

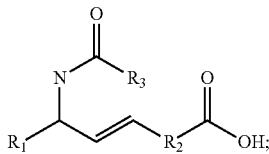

and

G. reacting the carboxylic acid with a nitroxide-containing compound comprising one of a hydroxyl or amine in a condensation reaction to produce the antioxidant compound, for example

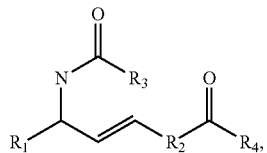

wherein $R_4$ is —NH—$R_4$ or —O—$R_4$, and $R_4$ is an —N—O., —N—OH or N═O containing group, such as described above.

Certain embodiments of the compounds disclosed herein also be synthesized following the procedures described in US 2010/0035869, which is incorporated herein by reference.

The compounds disclosed herein may also be coupled to a detector label moiety. The coupling may be affected by any method such as chemical conjugation techniques. Examples of detector label moieties include various enzymes, prosthetic groups, fluorescent materials, luminescent materials, bioluminescent materials, and radioactive materials. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin. The term "fluorophore" as used herein refers to a composition that is inherently fluorescent or demonstrates a change in fluorescence upon binding to a compound or metal ion, i.e., fluorogenic. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol. The term "label," as used herein, refers to a chemical moiety or protein that is directly or indirectly detectable (e.g. due to its spectral properties, conformation or activity) when attached to a target or compound and used in the present methods, including reporter molecules and carrier molecules. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a colorimetric substrate (e.g., tetramethylbenzidine (TMB)) or a fluorogenic substrate such as Amplex Red reagent (Molecular Probes, Inc.) to detect the presence of HRP.

A fluorophore used in the methods and compositions described herein, can contain one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

For example, a fluorophore may be any chemical moiety that exhibits an absorption maximum at wavelengths greater than 280 nm, and retains its spectral properties when covalently attached to a modified nucleotide such as, by way of example only, an azide, and alkyne or a phosphine. Fluorophores include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Xanthene type fluorophores include, but are not limited to, a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276; 5,846,737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). In certain embodiments, the fluorophore is a xanthene that is bound via a linkage that is a single covalent bond at the 9-position of the xanthene. In other embodiments, the xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Illustrative targeted nitroxide agents include:

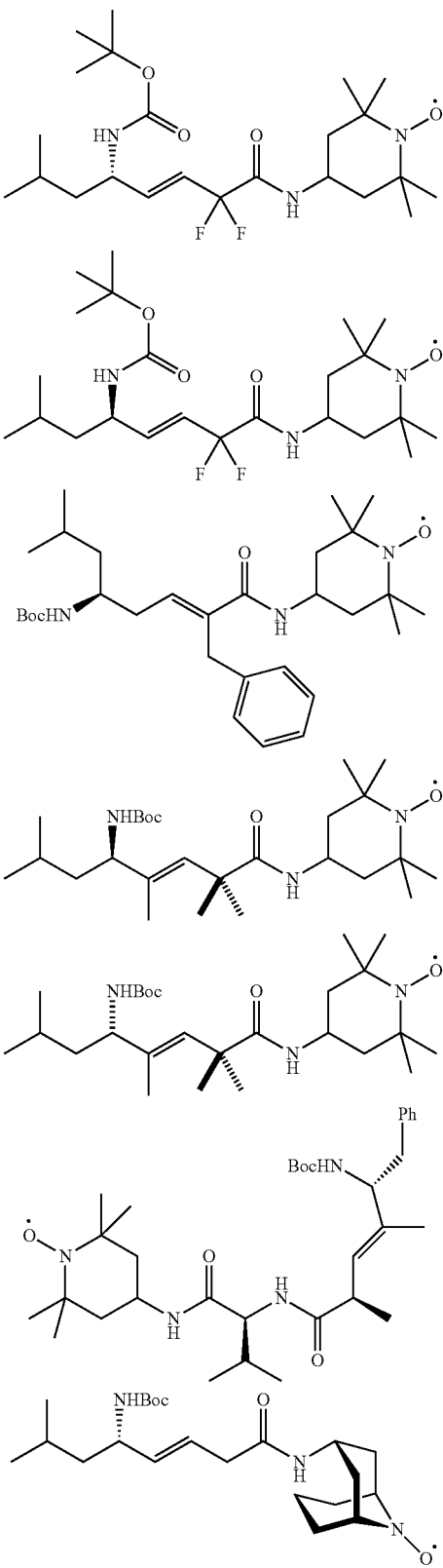

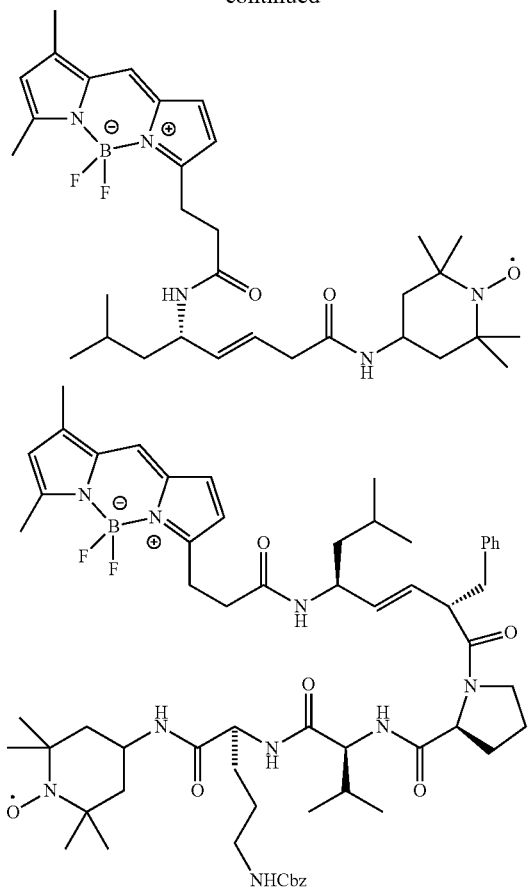

Methods of Use and Pharmaceutical Compositions

In a therapeutic embodiment, a method of scavenging free-radicals in a subject (e.g., a patient in need of treatment with a free-radical scavenger) is provided, comprising administering to the subject an amount of one or more compound described herein and having a free-radical scavenging group, such as a nitroxide-containing group effective to scavenge free radicals. As described above, a number of diseases, conditions or injuries can be ameliorated or otherwise treated or prevented by administration of free radical scavenging compounds, such as those described herein.

Any agent or agents used for prevention, mitigation or treatment in a subject of injury caused by radiation exposure may be administered in an amount effective to prevent, mitigate of treat such injury, namely in an amount and in a dosage regimen effective to prevent injury or to reduce the duration and/or severity of the injury resulting from radiation exposure. According to one non-limiting embodiment, an effective dose ranges from 0.1 or 1 mg/kg to 100 mg/kg, including any increment or range therebetween, including 1 mg/kg, 5 mg/kg, 10 mg/kg, 20 mg/kg, 25 mg/kg, 50 mg/kg, and 75 mg/kg. However, for each compound described herein, an effective dose or dose range is expected to vary from that of other compounds described herein for any number of reasons, including the molecular weight of the compound, bioavailability, specific activity, etc. The therapeutic window between the minimally-effective dose, and maximum tolerable dose in a subject can be determined empirically by a person of skill in the art, with end points being determinable by in vitro and in vivo assays, such as those described herein and/or are acceptable in the pharmaceutical and medical arts for obtaining such information regarding radioprotective agents. Different concentrations of the agents described herein are expected to achieve similar results, with the drug product administered, for example and without limitation, once prior to an expected radiation dose, such as prior to radiation therapy or diagnostic exposure to ionizing radiation, during exposure to radiation, or after exposure in any effective dosage regimen. The compounds can be administered continuously, such as intravenously, one or more times daily, once every two, three, four, five or more days, weekly, monthly, etc., including increments therebetween. A person of ordinary skill in the pharmaceutical and medical arts will appreciate that it will be a matter of simple design choice and optimization to identify a suitable dosage regimen for prevention, mitigation or treatment of injury due to exposure to radiation.

The compounds described herein also are useful in preventing, mitigating (to make less severe) and/or treating injury caused by radiation exposure. By radiation, in the context of this disclosure, it is meant types of radiation that result in the generation of free radicals, e.g., reactive oxygen species (ROS), as described herein. The free radicals are produced, for example and without limitation, by direct action of the radiation, as a physiological response to the radiation and/or as a consequence of damage/injury caused by the radiation. In one embodiment, the radiation is ionizing radiation. Ionizing radiation consists of highly-energetic particles or waves that can detach (ionize) at least one electron from an atom or molecule. Examples of ionizing radiation are energetic beta particles, neutrons, and alpha particles. The ability of light waves (photons) to ionize an atom or molecule varies across the electromagnetic spectrum. X-rays and gamma rays can ionize almost any molecule or atom; far ultraviolet light can ionize many atoms and molecules; near ultraviolet and visible light are ionizing to very few molecules. Microwaves and radio waves typically are considered to be non-ionizing radiation, though damage caused by, e.g., microwaves, may result in the production of free-radicals as part of the injury and/or physiological response to the injury.

The compounds typically are administered in an amount and dosage regimen to prevent, mitigate or treat the effects of exposure of a subject to radiation. The compounds may be administered in any manner that is effective to treat, mitigate or prevent damage caused by the radiation. Examples of delivery routes include, without limitation: topical, for example, epicutaneous, inhalational, enema, ocular, otic and intranasal delivery; enteral, for example, orally, by gastric feeding tube and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral, intravenous, intramuscular and transdermal approaches being preferred in many instances.

The compounds may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

In one embodiment, the dosage form is a transdermal device, or "patch". The general structure of a transdermal patch is broadly known in the pharmaceutical arts. A typical patch includes, without limitation: a delivery reservoir for containing and delivering a drug product to a subject, an occlusive backing to which the reservoir is attached on a proximal side (toward the intended subject's skin) of the backing and extending beyond, typically completely surrounding the reservoir, and an adhesive on the proximal side of the backing, surrounding the reservoir, typically completely, for adhering the patch to the skin of a patient. The reservoir typically comprises a matrix formed from a nonwoven (e.g., a gauze) or a hydrogel, such as a polyvinylpyrrolidone (PVP) or polyvinyl acetate (PVA), as are broadly known. The reservoir typically comprises the active ingredient absorbed into or adsorbed onto the reservoir matrix, and skin permeation enhancers. The choice of permeation enhancers typically depends on empirical studies. Certain formulations that may be useful as permeation enhancers include, without limitation: DMSO; 95% Propylene Glycol+ 5% Linoleic Acid; and 50% EtOH+40% HSO+5% Propylene Glycol+5% Brij30

EXAMPLES

Example 1

Difluorinated Compound

Figure 3:
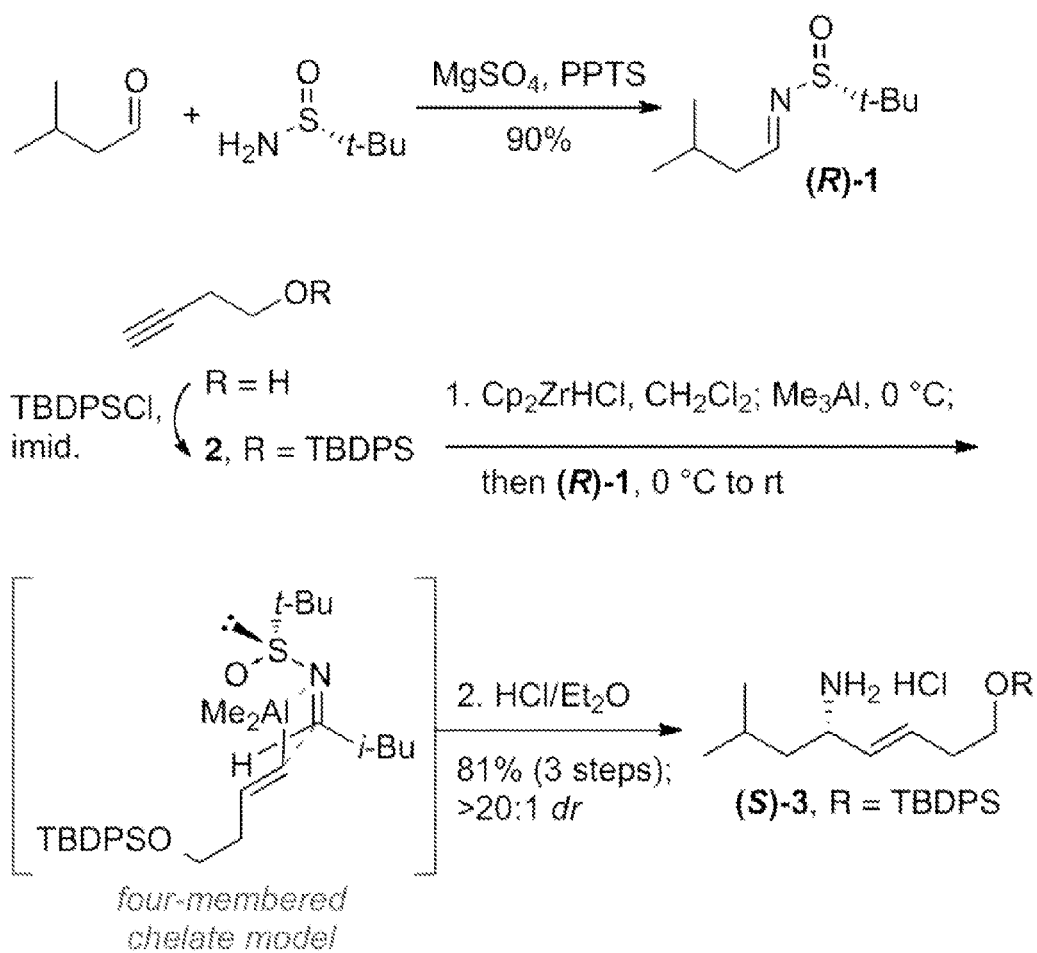

A difluorinated analog of JP4-039 was envisioned to enhance the bioavailability of the agent. Hydrozirconation of alkyne 2 with Cp$_2$ZrHCl, followed by transmetalation to trimethylaluminum and subsequent addition to chiral sulfinimine (R)-1 provided a diastereomerically pure (>20:1 dr) allylic amine according to $^1$H NMR analysis of the crude reaction mixture (see FIG. 3). A four-membered chelate model has been proposed to account for this excellent diastereoselectivity. Treatment of the crude reaction mixture with HCl in diethyl ether yielded the amine hydrochloride (S)-3 on multigram scale and in 81% yield over 3 steps from 3-butyn-1-ol. The N-tert-butylsulfinimine (R)-1 could be easily obtained from isovaleraldehyde in 90% yield and proved remarkably stable to storage.

We were able to use the allylic amine (S)-3 as a linchpin intermediate for the preparation of various compounds. Thus, acylation of amine (S)-3 with either a Boc, Cbz or diphenylphosphinoyl group, followed by TBAF-mediated deprotection of the silyl ether, afforded the alcohols (S)-5a-c (see FIG. 4). Jones oxidation to the corresponding carboxylic acids and final coupling with 4-AT using the EDCUHOBt/DMAP protocol provided the desired alkene isosteres (S)-6a-c in moderate to good yields.

The methyl ester (S)-11, prepared from alcohol (S)-5a, was treated with 3 equiv. of the fluorinating agent N-fluoro-N-(phenylsulfonyl)benzenesulfonamide (accufluor, NFSi) and 2.3 equiv. of NaHMDS in THF at −78° C. to afford the desired difluoroester (S)-12 in 86% yield. Saponification with tetrabutylammonium hydroxide (TBAH) and condensation with 4-AT provided the difluoro derivative (S)-13 in good yield (see FIG. 5).

Example 2

ABNO Compound

Preparation of 3-amino-ABNO (12) was envisioned from the known ketone 21, which was easily accessible in one step from acetonedicarboxylic acid and glutaraldehyde (Scheme 1). Conversion of 21 to oxime 22, followed by reduction to the amine with nickel boride and N-Boc protection provided carbamate 23 in high yield. Removal of the benzyl group by catalytic hydrogenolysis and oxidation of the free secondary amine in the presence of urea-hydrogen peroxide complex (UHP) furnished the Boc-protected nitroxide 24. However, once the Boc group was removed, the resulting 3-amino-ABNO (12) was found to be unstable, thus preventing its use in the coupling step with 15a, the carboxylic acid derived from 15.

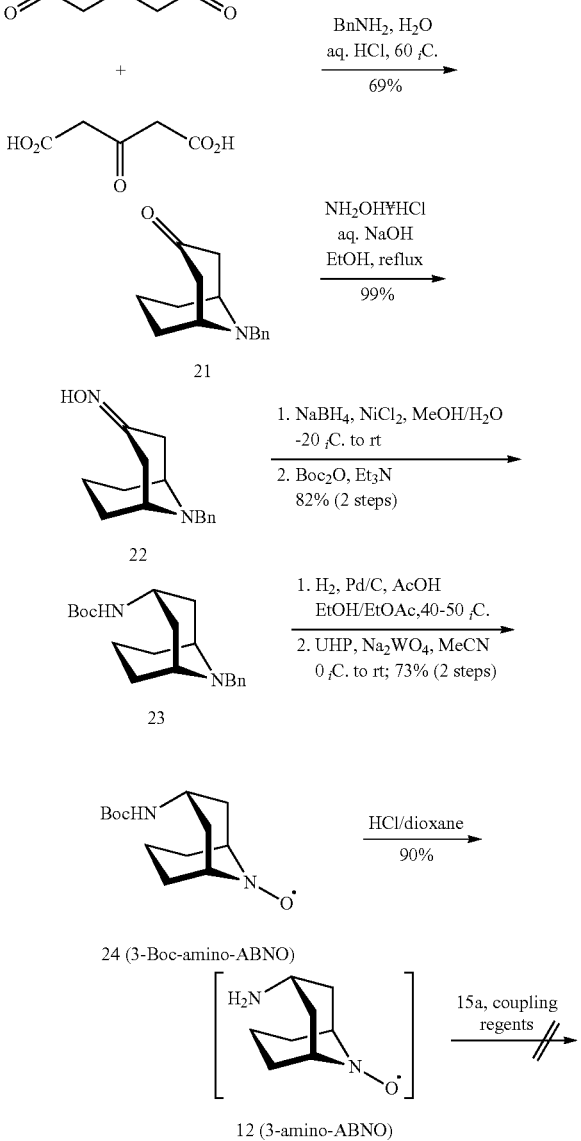

Scheme 1. Synthesis of the unstable nitroxide 12 (3-amino-ABNO).

To avoid the stability problem of 12, the synthetic route to obtain this ABNO analog was modified so that the nitroxide could be formed in the last step after N-acylation. Reduction of oxime 22 and EDCI coupling of the resulting primary amine with acid 15a were readily accomplished and gave amide 25 in 57% yield over 3 steps (Scheme 2). Benzyl amine cleavage with ceric ammonium nitrate (CAN), followed by UHP-assisted oxidation to the nitroxide then provided the desired ABNO analog 26 in 69% yield.

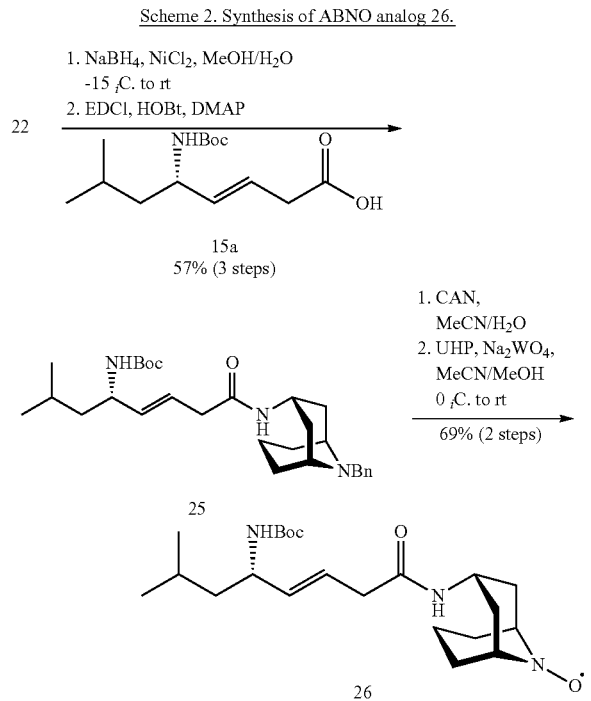

The synthesis of ABNO compound 26 is described below in more detail.

tert-Butyl 9-benzyl-9-azabicyclo[3.3.1]nonan-3-ylcarbamate (23). A suspension of oxime 22 (1.30 g, 5.34 mmol) and NiCl$_2$ (69.2 mg, 0.534 mmol) in MeOH (25 mL) was treated at −20° C. with NaBH$_4$ (2.13 g, 53.4 mmol) portionwise. The resulting dark mixture was vigorously stirred between −20 and −10° C. under argon. After 1.5 h, a solution of NaBH$_4$ (1.70 g, 42.7 mmol) in water (5 mL) was added. The reaction mixture was stirred at the same temperature for 1.5 h, then warmed to rt. After stirring for 1 h at rt, the mixture was quenched carefully with acetone, then filtered over Celite and the brown solid rinsed with MeOH. The solution was concentrated in vacuo, and the residue was taken up in water, acidified with 6 N aq. HCl (pH<2), extracted twice with Et$_2$O, then basified with solid NaOH (pH>9) and extracted twice with CHCl$_3$. An emulsion formed with a white precipitate that was filtered over Celite. The combined chloroformed layers were washed with brine, dried (K$_2$CO$_3$), filtered and concentrated in vacuo to afford 1.49 g of the crude amine as a pale yellow oil that was carried on to the next step without further purification.

To a solution of this amine in dry CH$_2$Cl$_2$ (100 mL) were added Et$_3$N (2.25 mL, 16.0 mmol) and then Boc$_2$O (1.29 g, 5.87 mmol) at 0° C. The reaction mixture was stirred at rt under argon for 18 h, then quenched with sat. aq. NH$_4$Cl and the aqueous phase extracted with CH$_2$Cl$_2$. The combined organic layers were dried (Na$_2$SO$_4$), filtered and concentrated in vacuo. The residue was taken up in CH$_2$Cl$_2$, and the insoluble material filtered to afford 481 mg of a first crop of product as a white powder. Chromatography of the mother liquor on SiO$_2$ (9:1 to 5:5, hexanes/EtOAc) afforded 4 other fractions of different purity for a total amount of 964 mg. The total amount of title compound obtained was ca. 1.44 g (82%, 2 steps). A fraction of product was recrystallized in EtOH (ca. 4 mL) to afford colorless crystals. $^1$H NMR showed a 3:1 mixture of stereoisomers: mp 153.6-155.0° C. (EtOH); IR (neat) 3312 (br), 3023, 2988, 2971, 2943, 2911, 2861, 2846, 2826, 2809, 1672, 1532, 1493, 1472, 1450, 1387, 1364, 1316, 1303, 1290, 1282, 1254, 1228, 1185, 1169, 1133, 1068, 1046, 1029, 1018, 874, 837, 766, 736, 699, 671 cm$^{-1}$; $^1$H NMR (CDCl$_3$, 300 MHz) δ 7.40-7.18 (m, 5 H), 4.40-4.24 (m, 1 H), 4.24-4.00 (m, 1H), 3.82 (s, 2 H), 3.07 (bd, 2 H, J=11.1 Hz), 2.38 (ddd, 2 H, J=12.0, 12.0, 6.3 Hz), 1.93 (d, 2 H, J=6.3 Hz), 1.60-1.50 (m, 2 H), 1.46 (s, 9 H), 1.15 (app td, 2 H, J=11.0, 3.0 Hz), 0.99 (app bd, 2 H, J=6.6 Hz); $^{13}$C NMR (CDCl$_3$, 100 MHz) δ 155.5, 140.7, 128.5, 128.4, 126.9, 79.2, 56.0, 49.4, 42.9, 34.2, 28.7, 24.8, 14.5; ESI-MS 331 ([M+H]$^+$, 100), 275 ([M-t-Bu+H]$^+$, 93); HRMS (ESI) m/z calcd for C$_{20}$H$_{31}$N$_2$O$_2$ (M+H) 331.2386. found 331.2392.

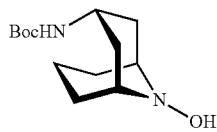

3-(tert-Butoxycarbonylamino)-9-azabicyclo[3.3.1] nonane N-oxyl (3-Boc-amino-ABNO, 24). A flask containing a suspension of the Bn-protected amine 24 (715 mg, 2.16 mmol) and AcOH (5 drops) in 10:1 EtOH/EtOAc (30 mL) was purged and filled 3 times with argon, then 10% Pd/C (143 mg) was added. The flask was purged and filled 3 times with H$_2$, and the resulting black suspension was stirred at 40-50° C. under H$_2$ (1 atm) for 3 h. The reaction mixture was then filtered through a pad of Celite, the Celite washed with EtOAc and MeOH, and the solution concentrated in vacuo to afford 591 mg of the crude amine as a white powder, that was carried on to the next step without further purification.

To a suspension of this amine (755 mg, 3.14 mmol) in MeCN (3.1 mL) was added Na$_2$WO$_4$.2H$_2$O (523 mg, 1.57 mmol) and the mixture was stirred at rt for 30 min. After cooling to 0° C., UHP (1.52 g, 15.7 mmol) was added and the reaction mixture was stirred at 0° C. for 1 h, then allowed to warm to rt. After stirring for 3.5 h at rt, water was added and the resulting mixture was extracted with CHCl$_3$ (3×). The combined organic layers were dried (K$_2$CO$_3$), filtered and concentrated in vacuo. The residue was taken up in EtOH, and the insoluble material filtered to afford 467 mg of a first crop of product as a yellow powder. Chromatography of the mother liquor on SiO$_2$ (8:2 to 4:6, hexanes/EtOAc) afforded 120 mg of a second crop as a yellow powder. The total amount of title compound obtained was 587 mg (73%, 2 steps): mp 222.8° C. (sublimation); IR (neat) 3334 (br), 2969, 2947, 2870, 1677, 1525, 1389, 1366, 1351, 1307, 1292, 1273, 1252, 1232, 1225, 1167, 1131, 1116, 1068, 1046, 1036, 1019, 869, 846, 826, 779, 770, 753 cm$^{-1}$; ESI-MS m/z 298 ([M$_{red}$+MeCN+H]$^+$, 30), 278 ([M+Na]$^+$, 63), 275 (54), 263 (100), 257 ([M$_{red}$+H]$^+$, 20), 241 ([M-O+H]$^+$, 23), 222 (50), 212 (28); HRMS (ESI) m/z calcd for C$_{13}$H$_{23}$N$_2$O$_3$Na (M+Na) 278.1606. found 278.1593.

A sample of this nitroxide (20.0 mg, 0.0783 mmol) was suspended in MeOH (0.8 mL) and L-ascorbic acid (13.9 mg, 0.0783 mmol) was added. The slightly yellow suspension became white within a few seconds. After stirring at rt for 40 min under argon, the solvent was removed in vacuo. The resulting residue was taken up in EtOAc and sonicated. The insoluble material was filtered, rinsed with EtOAc and MeOH, and dried, to yield 15.0 mg (75%) of the corresponding hydroxylamine as a white solid. Representative experimental data are as follows: $^1$H NMR (DMSO-$d_6$, 400 MHz, 2:1 mixture of isomers) δ 7.93 (s, 0.8 H), 7.43 (s, 0.4 H), 6.57 (d, 0.4 H, J=8.0 Hz), 6.45 (d, 0.7 H, J=8.8 Hz), 4.40-4.25 (m, 0.8 H), 3.85-3.70 (m, 0.4 H), 3.40-3.20 (m, 1 H), 3.20-3.10 (m, 1 H), 2.23-2.02 (m, 2 H), 2.02-1.80 (m, 2 H), 1.70-1.53 (m, 2 H), 1.37 (s, 9 H), 1.25-1.14 (m, 1 H), 1.08 (app bt, 2 H, J=11.2 Hz), 0.82 (app bd, 1 H, J=11.6 Hz); $^{13}$C NMR (DMSO-$d_6$, 100 MHz, mixture of isomers) δ 154.8, 77.3, 77.1, 55.2, 53.3, 40.4, 33.2, 32.2, 30.8, 28.3, 28.1, 23.4, 13.0, 12.3.

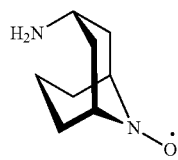

12

3-Amino-9-azabicyclo[3.3.1]nonane N-oxyl (3-amino-ABNO, 12) A mixture of Boc-protected amine 3-Boc-amino-ABNO (24, 200 mg, 0.783 mmol) in a 4.0 N solution of HCl in 1,4-dioxane (3.3 mL, 13.2 mmol) was stirred at 0° C. for 1 h and at rt for an additional 2 h. The suspension was then filtered and the solid rinsed with cold dry Et$_2$O, to give 167 mg of an off-white powder. It was dissolved in a minimum of 2.5 N aq. NaOH, and extracted with warm CHCl$_3$ (7×). The combined organic layers were dried (K$_2$CO$_3$), filtered and concentrated in vacuo to afford 110 mg (90%) of a red oil. Upon high vacuum and/or storage at rt for not more than 1 h, the product started to loose the red color characteristic for a nitroxide and became pale yellow. Thus, the title compound is unstable.

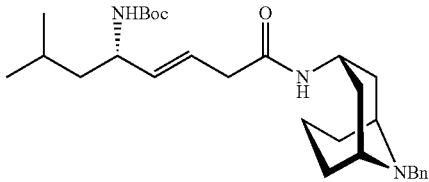

25 tert-Butyl(S,E)-8-(9-benzyl-9-azabicyclo[3.3.1]nonan-3-ylamino)-2-methyl-8-oxooct-5-en-4-ylcarbamate (25). A suspension of oxime 22 (400 mg, 1.64 mmol) and NiCl$_2$ (21.2 mg, 0.164 mmol) in MeOH (8 mL) was treated at −15° C. with NaBH$_4$ (652 mg, 16.4 mmol) portionwise. The resulting dark mixture was vigorously stirred between −15 and 0° C. under argon. After 1.5 h, a solution of NaBH$_4$ (326 mg, 8.18 mmol) in water (1 mL) was added. The reaction mixture was stirred from 0° C. to rt. After 1 h, the reaction mixture was quenched carefully with acetone, then filtered over Celite and the brown solid rinsed with MeOH. The solution was concentrated in vacuo, and the residue was taken up in water, acidified with 6 N aq. HCl (pH<2), extracted twice with Et$_2$O, then basified with solid NaOH (pH>9) and extracted with CHCl$_3$ (3×). The combined chloroformed layers were dried (Na$_2$SO$_4$), filtered and concentrated in vacuo to afford 416 mg of the crude amine as a yellow oil that was carried on to the next step without further purification.

To a solution of acid 15a (424 mg, 1.52 mmol, crude) in dry CH$_2$Cl$_2$ (18 mL) at 0° C. were added successively HOBt.H$_2$O (246 mg, 1.82 mmol), DMAP (206 mg, 1.67 mmol), a solution of this amine (403 mg, 1.59 mmol, crude) in dry CH$_2$Cl$_2$ (2 mL), and EDCI (356 mg, 1.82 mmol). The resulting mixture was stirred at rt under argon for 14 h, then washed with 2.5 N aq. NaOH (3×). The organic layer was dried (Na$_2$SO$_4$), filtered and concentrated in vacuo. Chromatography on SiO$_2$ (8:2 to 4:6, hexanes/EtOAc) afforded 421 mg (57%, 3 steps) of the title compound as a white powder: mp 115.0-115.4° C.; $[\alpha]_D^{23}$+12.6 (c 1.0, CH$_2$Cl$_2$); IR (neat) 3338 (br), 3277 (br), 2924, 2867, 1681, 1635, 1519, 1495, 1467, 1452, 1435, 1389, 1364, 1349, 1327, 1307, 1277, 1252, 1163, 1137, 1081, 1060, 1044, 1025, 1010, 993, 964, 930, 874, 842, 760, 742, 703 cm$^{-1}$; $^1$H NMR (CDCl$_3$, 400 MHz) δ 7.39-7.34 (m, 2 H), 7.33-7.27 (m, 2 H), 7.25-7.19 (m, 1 H), 5.95-5.80 (m, 1 H), 5.66 (dt, 1 H, J=15.2, 7.2 Hz), 5.46 (dd, 1 H, J=15.4, 6.6 Hz), 4.55-4.45 (m, 1 H), 4.41 (ddddd, 1 H, J=12.0, 12.0, 8.4, 6.0, 6.0 Hz), 4.04 (app p, 1 H, J=7.2 Hz), 3.82 (s, 2 H), 3.08 (app bd, 2 H, J=10.4 Hz), 2.98 (d, 2 H, J=7.2 Hz), 2.40-2.26 (m, 2 H), 2.06-1.87 (m, 3H), 1.73-1.60 (m, 3 H), 1.58-1.49 (m, 1 H), 1.44 (s, 9 H), 1.34 (app td, 2 H, J=7.3, 1.4 Hz), 1.03-0.92 (m, 2 H), 0.93 (d, 3 H, J=6.8 Hz), 0.93 (d, 3 H, J=6.4 Hz); $^{13}$C NMR (CDCl$_3$, 100 MHz) δ 170.4, 155.6, 140.6, 137.2, 128.6, 128.4, 126.9, 123.6, 79.5, 56.0, 51.6, 49.3, 49.3, 44.2, 42.0, 40.4, 33.5, 33.4, 28.6, 24.8, 24.7, 22.7, 14.5; ESI-MS m/z 527 (80), 506 ([M+Na]$^+$, 84), 484 ([M+H]$^+$, 67); HRMS (ESI) m/z calcd for C$_{29}$H$_{45}$N$_3$O$_3$Na (M+Na) 506.3359. found 506.3336.

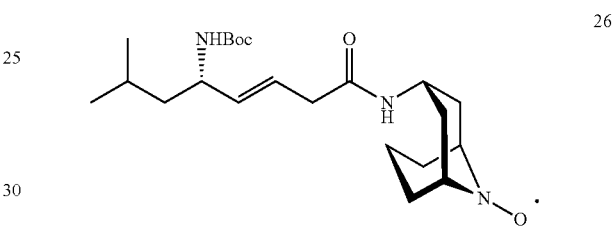

26

(S,E)-N-(9-Azabicyclo[3.3.1]nonan-9-oxo-3-yl)-5-(tert-butoxycarbonylamino)-7-methyloct-3-enamide (26). A solution of Bn-protected amine 25 (150 mg, 0.309 mmol) in 5:1 MeCN/H$_2$O (12 mL) was treated with CAN (339 mg, 0.618 mmol). The resulting red reaction mixture was stirred at rt under argon. After 3.5 h, more CAN (170 mg, 0.309 mmol) was added. After 19 h stirring, sat. aq. NaHCO$_3$ (12 mL) was added and stirring was continued for 15 min. The mixture was then extracted with CHCl$_3$ (3×50 mL). The combined organic layers were washed with brine, dried (Na$_2$SO$_4$), filtered and concentrated in vacuo to yield 144 mg of the crude amine as a brownish residue, that was carried on to the next step without further purification.

To a suspension of this amine (140 mg, 0.301 mmol) in 1:1 MeCN/MeOH (1.2 mL) was added Na$_2$WO$_4$.2H$_2$O (50.2 mg, 0.151 mmol) and the mixture was stirred at rt for 30 min. After cooling to 0° C., UHP (146 mg, 1.51 mmol) was added and the reaction mixture was stirred at 0° C. for 1 h, then allowed to warm to rt and stirred overnight. After 17 h, water was added and the resulting mixture was extracted twice with CHCl$_3$. The combined organic layers were dried (K$_2$CO$_3$), filtered and concentrated in vacuo. Chromatography on SiO$_2$ (5:5, hexanes/EtOAc to EtOAc) afforded 84.9 mg (69%, 2 steps) of the title compound as orange microcrystals formed from an initial red oil. Representative experimental data are as follows: mp 140.2-141.0° C. (EtOAc); $[\alpha]_D^{23}$+25.9 (c 1.0, CH$_2$Cl$_2$); IR (neat) 3292 (br), 2949, 2926, 2867, 1690, 1657, 1539, 1469, 1448, 1400, 1389, 1362, 1325, 1308, 1284, 1269, 1247, 1221, 1167, 1116, 1088, 1070, 1040, 1018, 977, 678 cm$^{-1}$; ESI-MS m/z 431 ([M+Na]$^+$, 77); HRMS (ESI) m/z calcd for C$_{22}$H$_{38}$N$_3$O$_4$Na (M+Na) 431.2760. found 431.2736.

A sample of this nitroxide (10.0 mg, 0.0245 mmol) was dissolved in MeOH (0.3 mL) and L-ascorbic acid (4.4 mg, 0.0245 mmol) was added. The pale orange suspension became colorless within a few seconds. After stirring at rt for 30 min under argon, the solvent was removed in vacuo. The resulting residue was dissolved in CH₂Cl₂ with some MeOH and washed twice with water. The combined aqueous layers were extracted with warm CH₂Cl₂ (4×), and the combined organic layers were dried (Na₂SO₄), filtered and concentrated in vacuo to yield 9.4 mg (94%) of the corresponding hydroxylamine as a white powder: $^1$H NMR (CDCl₃, 400 MHz, 3:1 mixture of isomers) δ 6.02-5.91 (m, 0.25H), 5.82 (app bd, 0.75H, J=6.0 Hz), 5.71-5.58 (m, 1 H), 5.52-5.41 (m, 1 H), 4.84 (ddddd, 0.75H, J=11.6, 11.6, 6.8, 6.8, 6.8 Hz), 4.52 (app bs, 1 H), 4.23 (app o, 0.25H, J=6.2 Hz), 4.09-3.97 (m, 1 H), 3.57 (app bd, 1.5 H, J=9.6 Hz), 3.42 (app bd, 0.5 H, J=10.0 Hz), 3.00-2.91 (m, 2 H), 2.51-2.38 (m, 0.6 H), 2.38-2.19 (m, 2 H), 2.05-1.88 (m, 0.5 H), 1.80-1.57 (m, 3 H), 1.56-1.46 (m, 2 H), 1.44 (s, 9 H), 1.34 (app td, 2 H, J=7.3, 1.8 Hz), 1.38-1.26 (m, 1H), 1.14 (app bt, 2 H, J=12.4 Hz), 0.93 (d, 3 H, J=6.8 Hz), 0.92 (d, 3 H, J=6.8 Hz); $^{13}$C NMR (CDCl₃, 100 MHz, mixture of isomers) δ 170.6, 170.4, 155.6, 137.4, 137.3, 123.6, 123.5, 79.4, 55.9, 55.9, 54.1, 51.6, 51.5, 44.2, 40.3, 40.3, 39.7, 33.8, 33.8, 32.5, 31.2, 31.1, 29.9, 28.6, 24.8, 23.6, 22.9, 22.7, 14.3, 13.5, 12.8.

Example 3

Labeled Compound

In order to more thoroughly investigate the ability of these nitroxides to partition in tissue and cells, and localize in mitochondria, a fluorescence-based visualization tool would be useful. A BODIPY®-FL fluorophore was selected as an example for this purpose. Analogs of JP4-039 and XJB-5-131 with a BODIPY®-FL label in place of the N-Boc group were synthesized as shown in Schemes 3 and 4.

The direct synthesis of the labeled derivative from JP4-039 failed, since, after the Boc group of JP4-039 was successfully removed with HCl, treatment of the free amine with the N-hydroxysuccinimide activated ester of BODIPY®-FL (BODIPY®-FL-NHS) provided an 83:17 mixture of the undesired bis-coupling product 36 and the desired 35 based on HPLC/UV analysis of the crude reaction product (Scheme 3). In an alternative strategy, we planned to attach the BODIPY®-FL label to the alkene peptide isostere scaffold prior to coupling to the 4-AT group. Accordingly, carboxylic acid 15a was protected as the methyl ester to give 37. Removal of the Boc-protecting group with TFA followed by coupling to BODIPY®-FL-NHS provided 38 in 82% yield. Saponification of the methyl ester under standard basic conditions resulted in extensive decomposition; therefore, pig liver esterase (PLE) in acetone/pH 7 phosphate buffer was used to effect a chemoselective transformation. Coupling of the resulting acid to 4-AT provided the desired BODIPY®-FL-labeled compound 35 in 56% yield over 2 steps.

The fluorophore-tagged XJB-5-131 analog 40 was synthesized from intermediate 19 in an analogous fashion to 35 (Scheme 4). Removal of the Boc-protecting group with TFA and subsequent coupling to BODIPY®-FL-NHS afforded 39 in 88% yield. Unfortunately, in the case of methyl ester 39, both standard basic saponification as well as PLE conditions that had been employed in the synthesis of the JP4-039 analog failed to provide the desired carboxylic acid. Accordingly, Me₃SnOH was used to affect this transformation. Coupling of the resulting carboxylic acid to 4-AT led to the BODIPY®-FL-labeled XJB-5-131 analog 40.

Scheme 3. Synthesis of the BODIPY®-FL labeled JP4-039 analog 35.

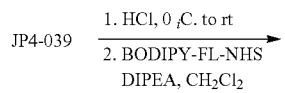

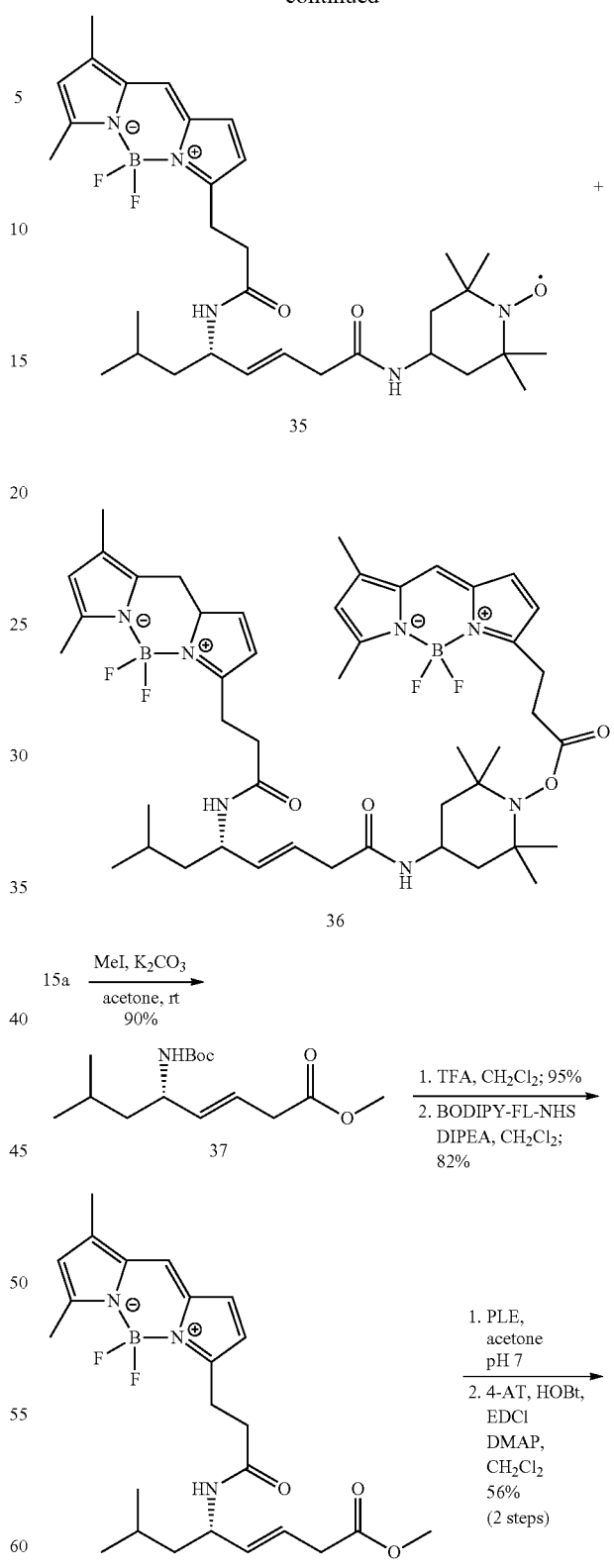

Scheme 4. Synthesis of the BODIPY®-FL-labeled XJB-5-131 analog 40.

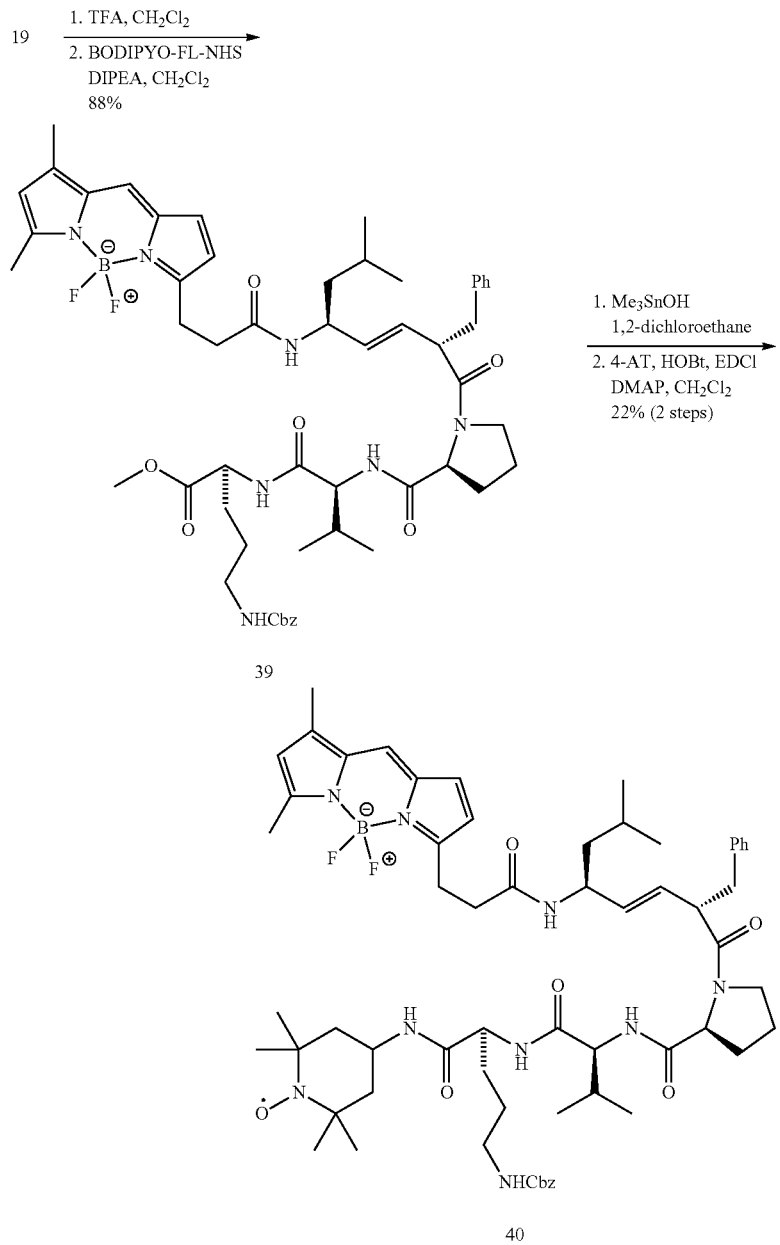

Example 4

Free Radical Reduction and Oxidizing Agent Evaluations of Compounds

The free radical reduction abilities of the nitroxides and nitroxide-conjugates were benchmarked by the DPPH (2,2-diphenyl-1-picrylhydrazyl) assay. For most compounds, the corresponding hydroxylamines were tested and, as expected, showed better scavenging properties due to their strong H-atom donor capacities, with $EC_{50}$ values comparable to those of the reference compounds ascorbic acid and curcumin (Table 2). For example, the 4-AT conjugates XJB-5-131 and JP4-039 did not exhibit any significant activity in the DPPH assay as the nitroxides; however, the potencies of their hydroxylamine forms, XJB-5-131-H and JP4-039-H were only slightly lower than those of ascorbate and curcumin. All TEMPO derivatives had $EC_{50}$ values in a relatively narrow range from 50-80 µM. Similarly, the reduced ABNO derivatives and 1-Me-AZADO derivatives were also effective free radical scavengers and showed very little derivation from each other and the TEMPO hydroxylamines. In contrast, the TMIO derivatives had notably decreased H-atom donor capabilities and showed ca. 3-fold higher $EC_{50}$ values. Notably, the nitroxide conjugates 20, 26, and 32 exhibited slightly higher $EC_{50}$ values than their corresponding nitroxide substructures.

Taking into account the rather minor differences between TEMPO, ABNO, and 1-Me-AZADO hydroxylamines, the DPPH radical quenching effect can be ordered as follows: TMIO<TEMPO≈1-Me-AZADO≤ABNO. Hence, as expected, the moderate reactivity of TMIO in the hydroxylamine form was confirmed, but somewhat surprisingly the structural changes in the TEMPO, ABNO, and 1-Me-AZADO chemotypes did not significantly influence their H-atom donor potential in their reduced form toward a highly delocalized nitrogen-centered free radical. Furthermore, the organic fragments attached to the nitroxide building blocks had no influence on this model reaction.

In contrast to the DPPH assay, which mainly addresses the radical scavenging/reducing properties of nitroxides and hydroxylamines, the reaction of nitroxides with ascorbic acid benchmarks their ability to act as oxidizing agents in their conversion to hydroxylamines, which is important to their protective function as electron scavengers in the mitochondrial electron transport chain. The electron acceptor potentials of various nitroxides were thus benchmarked in the presence of low, medium, and high concentrations of the electron donor ascorbate (Table 3). ESR was used to detect the characteristic triplet of the nitroxide vs the doublet of ascorbate radicals (see supplementary information), and the disappearance of the former and appearance of the latter was measured over 8.5 min.

TABLE 2

DPPH radical scavenging effects.

| Nitroxide | Compound | $EC_{50}$ [μM] |
|---|---|---|
| — | Ascorbic acid | 28 ± 5[a] |
|  | Curcumin | 26 ± 1[a] |
| TEMPO | TEMPO-H | 79 ± 2 |
|  | JP4-039-H | 57 ± 2 |
|  | XJB-5-131-H | 63 ± 0.5 |
| TMIO | 8-H | 169 ± 7 |
|  | 20-H | 490 ± 18 |
| ABNO | 24-H | 53 ± 7[b] |
|  | 26-H | 123 ± 8 |
| 1-Me-AZADO | 32-H | 63 ± 2 |
|  | 33-H | 94 ± 3 |

The assays were performed in EtOH with 100 μM DPPH for 30 min at 37° C. $EC_{50}$ values are the result of one experiment (n = 1) run as a duplicate, unless otherwise mentioned.
[a]n = 3.
[b]n = 2.

TABLE 3

Ascorbic acid electron scavenging assay measuring the disappearance of the nitroxide ESR signal after 8.5 min.

| Nitroxide type | Compound | Signal Decrease (%) (a) | (b) | (c) |
|---|---|---|---|---|
| TEMPO | 9 (TEMPOL) | 35.7 | 81 | 100 |
|  | JP4-039 | 29.7 | 81.4 | ND |
|  | XJB-5-131 | 76.7 | 92.4 | ND |
|  | 6 | 58.4 | 94.1 | ND |
| TMIO | 8 (5-amino-TMIO) | ND | ND | 40.3 |
|  | 20 | ND | 15.5 | 77.4 |
| ABNO | 24 (3-Boc-amino-ABNO) | 100 | 100 | ND |
|  | 26 | 100 | 100 | ND |
| 1-Me-AZADO | 32 (6-Boc-amino-1-Me-AZADO) | 100 | 100 | ND |

Assays were performed with 0.5 μM nitroxide in 33 μL phosphate buffered saline (PBS), 150 μM diethylenetriaminepentaacetic acid (DTPA), and 35 μL DMSO in the presence of 35 μM (a), 280 μM (b), and 1.12 mM (c) ascorbate solution, and the corresponding $t_{1/2}$ were determined for an 8.5 min ESR scan. ND = not determined.

Irradiation survival assays were used to test the ability of selected nitroxide-conjugates to protect against, or mitigate, irradiation-induced damage of 32Dc13 murine hematopoietic cells. The results for TEMPO- (JP4-039; 35), TMIO- (20), ABNO- (26) and 1-Me-AZADO- (33) type nitroxides demonstrate that all structural classes are able to protect cells from multiple killing events if given 1 h before irradiation, as shown by their increased $D_0$ (Table 4).

TABLE 4

Irradiation survival curve parameters in 32Dc13 cells.

| | Before irradiation | | After irradiation | |
|---|---|---|---|---|
| Compounds | Do (Gy) | ñ | Do (Gy) | ñ |
| Control | 1.3 ± 0.1 | 1.0 ± 0.1 | 1.6 ± 0.2 | 1.1 ± 0.1 |
| JP4-039 | 2.3 ± 0.3 (p = 0.043) | 1.0 ± 0.1 | 1.2 ± 0.1 | 3.5 ± 0.2 (p = 0.0001) |
| 35 | 2.6 ± 0.5 (p = 0.048) | 1.2 ± 0.1 | 1.5 ± 0.2 | 4.5 ± 1.1 (p = 0.0026) |
| 20 | 1.8 ± 0.1 (p = 0.029) | 1.0 ± 0.1 | 1.4 ± 0.1 | 2.4 ± 0.2 (p = 0.003) |
| 26 | 3.1 ± 0.6 (p = 0.048) | 1.0 ± 0.1 | 1.3 ± 0.1 | 2.7 ± 0.7 (p = 0.088) |
| 33 | 2.6 ± 0.4 (p = 0.041) | 1.0 ± 0.1 | 1.3 ± 0.1 | 2.5 ± 0.3 (p = 0.0065) |

32Dc13 cells were incubated in the presence of 10 μM nitroxides for 1 h and then irradiated to doses ranging from 0 to 8 Gy, or the cells were irradiated and then placed in media containing the nitroxides. Cells were placed in methylcellulose, and incubated for 7 d at 37° C. in a $CO_2$ incubator. Colonies of >50 cells were counted and data analyzed using linear quadratic or single-hit, multi-target models.
[a]Control = untreated 32Dc13 cells When given shortly after irradiation, all agents were also able to mitigate cell damage, according to the increase observed in ñ.

Cell survival in irradiation studies depends on complex biochemical pathways, possibly accounting for the complex correlation of nitroxide structure and radiation mitigation properties. Irradiation-induced cell death results from an accumulation of events that individually are not able to kill the cell, but which become lethal when added together. To develop a firmer basis for studying structural modifications, we assayed the ability to rescue cellular senescence induced by oxidative stress in $Erccl^{-/-}$ MEFs as a function of test agents (Table 5).

TABLE 5

Cell proliferation $EC_{50}$ values in $Erccl^{-/-}$ MEFs.

| Nitroxide type | Compound | $EC_{50}$ [nM] |
|---|---|---|
| — | Curcumin | 1,000 |
| TEMPO | 9 (TEMPOL) | 228.8 ± 23.9 |
|  | JP4-039 | 210.2 ± 15.2 |
|  | JP4-039-H | 1.0 ± 0.3 |
|  | XJB-5-131 | 212.1 ± 5.1 |
|  | 1 | 589 |
|  | 2 | 332 |
|  | 3 | 70.4 |
|  | 4 | 231 |
|  | 5 | 200 |
|  | 6 | 7.6 ± 1.4 |
| TMIO | 8 (5-amino-TMIO) | <1 |
|  | 20 | 17.6 ± 1.4 |
| ABNO | 24 (3-Boc-amino-ABNO) | 40.0 |
|  | 26 | 11.8 ± 2.7 |
| 1-Me-AZADO | 32 (6-Boc-amino-1-Me-AZADO) | 62.2 |
|  | 33 | 5.3 ± 0.5 |

$Erccl^{-/-}$ MEFs completely lack a critical DNA repair factor, making these cells highly sensitive to genotoxic and oxidative stress. Growth of the $Erccl^{-/-}$ MEFs in 20% $O_2$ results in cellular senescence as measured by senescence associated β-gal, γ-H2AX staining and p16 protein levels. The ability to rescue senescence, as measured by an increase in cell number, correlates with the inhibition of oxidative stress. In this assay, curcumin was used as a negative control, since this antioxidant shows only very weak effects, possibly due to its limited ability to cross the cell membrane.

Compounds I-6 in Table 5 have the structures:

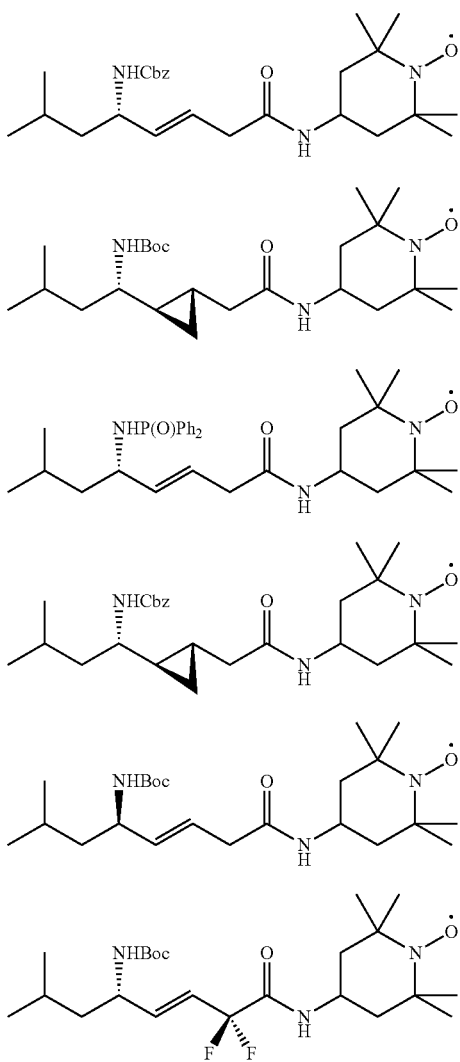

Other compounds in the above Tables have the structures:

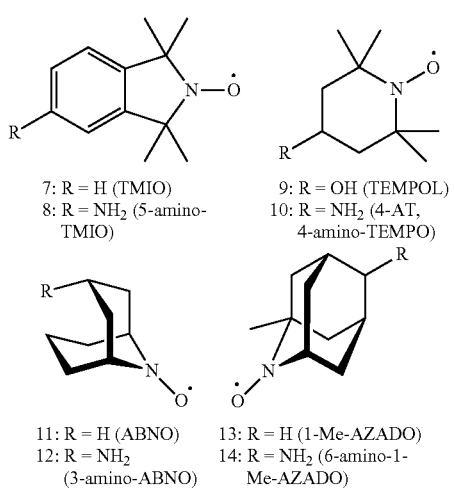

7: R = H (TMIO)
8: R = NH$_2$ (5-amino-TMIO)
9: R = OH (TEMPOL)
10: R = NH$_2$ (4-AT, 4-amino-TEMPO)
11: R = H (ABNO)
12: R = NH$_2$ (3-amino-ABNO)
13: R = H (1-Me-AZADO)
14: R = NH$_2$ (6-amino-1-Me-AZADO)

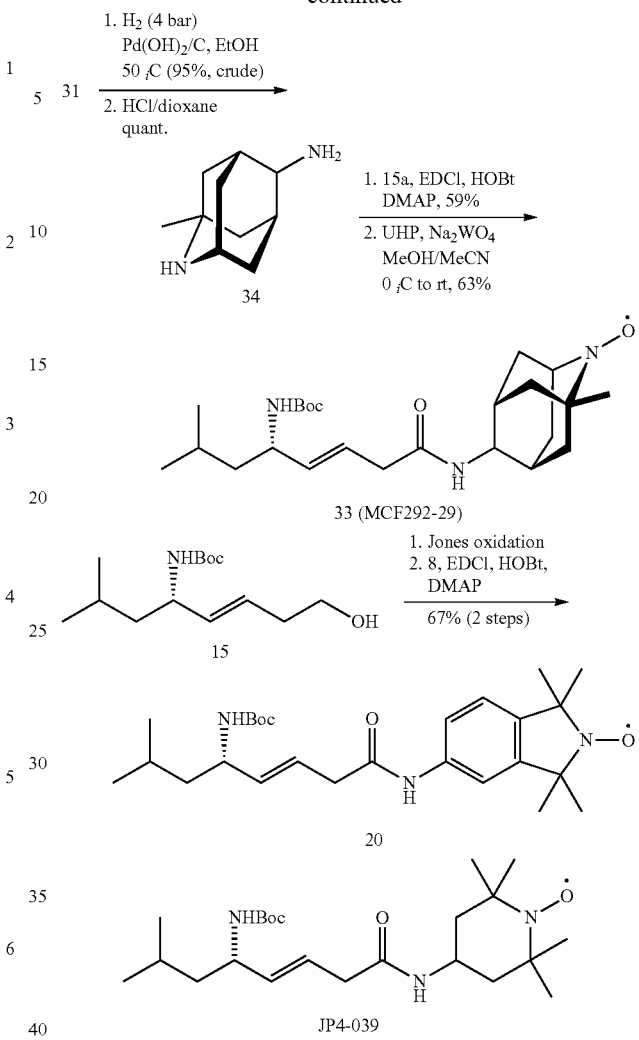

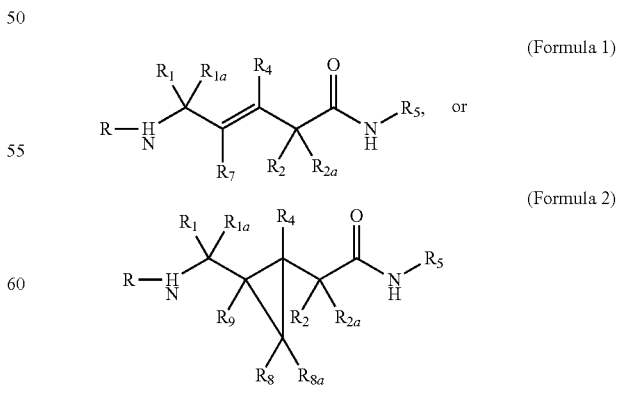

In view of the many possible embodiments to which the principles of the disclosed invention may be applied, it should be recognized that the illustrated embodiments are only preferred examples of the invention and should not be taken as limiting the scope of the invention.

What is claimed is:

1. A compound having a structure of:

(Formula 1)

(Formula 2)

wherein $R_1$ and $R_{1a}$ are independently hydrogen, a halo, $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_5$ is an —N—O., —N—OH or N=O containing group; R is —C(O)—$R_6$, —C(O)O—$R_6$, or —P(O)—$(R_6)_2$, wherein $R_6$ is $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted; $R_7$, $R_8$, $R_{8a}$, and $R_9$ are independently H or a halo; and $R_2$ and $R_{2a}$ are F.

2. The compound of claim 1, wherein $R_1$ is a $C_1$-$C_6$ straight or branched-chain alkyl; $R_{1a}$ is H; $R_7$ is H; $R_4$ is H; $R_5$ is an —N—O—. - containing group; and R is —C(O)O—$R_6$ wherein $R_6$ is $C_1$-$C_6$ straight or branched-chain alkyl.

3. The compound of claim 1, wherein the compound has a structure of:

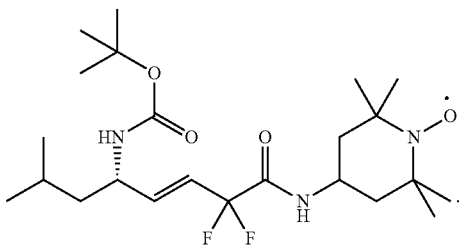

4. The compound of claim 1, wherein the compound has a structure of:

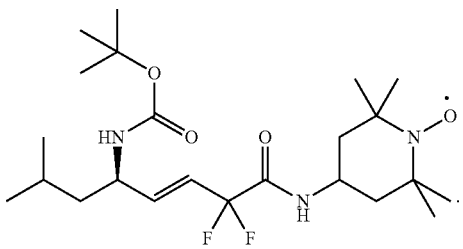

5. A compound having a structure of:

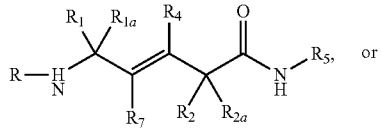

(Formula 1)

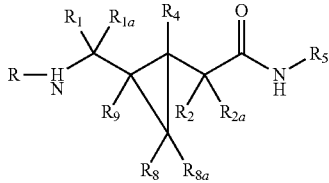

(Formula 2)

wherein $R_1$ and $R_{1a}$ are independently hydrogen, a halo, $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_5$ is an —N—O., —N—OH or N=O containing group; R is —C(O)—$R_6$, —C(O)O—$R_6$, or —P(O)—$(R_6)_2$, wherein $R_6$ is $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted; $R_8$, $R_{8a}$, and $R_9$ are independently H or a halo; $R_2$ and $R_{2a}$ are each a halo, $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; and $R_7$ is H, a halo, a $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted, provided that at least three of $R_2$, $R_{2a}$, $R_4$, and $R_7$ are not H.

6. The compound of claim 5, wherein $R_2$ and $R_{2a}$ are each a $C_1$-$C_6$ straight or branched-chain alkyl.

7. The compound of claim 6, wherein the compound has a structure of:

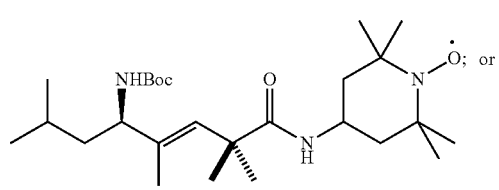

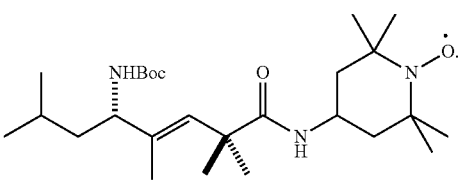

8. A compound having a structure of:

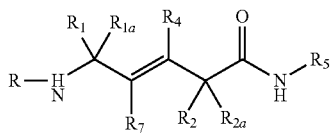
(Formula 1)

wherein $R_1$ is hydrogen, $R_{1a}$ is tert-butyl, 1-hydroxyethyl, isopropyl, or isobutyl: $R_2$, and $R_{2a}$ are each independently hydrogen $R_4$ is hydrogen; $R_5$ is

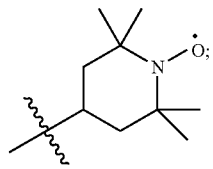

R is —C(O)O—$R_6$, wherein $R_6$ is tert-butyl; and $R_7$ is F or $CF_3$.

9. The compound of claim 1, further comprising a detector label moiety coupled to the compound, wherein the detector label moiety is selected from a fluorescent material, a luminescent material, a bioluminescent material, or a radioactive material.

10. The compound of claim 9, wherein the detector label moiety comprises a fluorophore covalently bonded to the compound.

11. The compound of claim 1, wherein the compound is in the form of a nitroxide, a hydroxylamine, or a nitroxonium ion.

12. The compound of claim 1, wherein the compound is in the form of a pharmaceutically acceptable salt or ester thereof.

13. A pharmaceutical composition comprising a compound of claim 1, and at least one pharmaceutically acceptable additive.

14. A pharmaceutical composition comprising a compound of claim 5, and at least one pharmaceutically acceptable additive.

15. A pharmaceutical composition comprising a compound of claim 8, and at least one pharmaceutically acceptable additive.

16. A pharmaceutical composition comprising a compound of claim 3, and at least one pharmaceutically acceptable additive.

17. A pharmaceutical composition comprising a compound of claim 4, and at least one pharmaceutically acceptable additive.

* * * * *